United States Patent
Wong et al.

(10) Patent No.: US 7,833,504 B2
(45) Date of Patent: Nov. 16, 2010

(54) SILYLATED CARBON NANOTUBES AND METHODS OF MAKING SAME

(75) Inventors: Stanislaus S. Wong, Stony Brook, NY (US); Tirandai Hemraj-Benny, Richmond Hill, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 12/229,905

(22) Filed: Aug. 27, 2008

(65) Prior Publication Data

US 2009/0060815 A1 Mar. 5, 2009

Related U.S. Application Data

(60) Provisional application No. 60/968,088, filed on Aug. 27, 2007.

(51) Int. Cl.
*C01B 33/00* (2006.01)
(52) U.S. Cl. .................. 423/324; 977/742; 977/749
(58) Field of Classification Search .......... 977/748, 977/847, 742, 749; 423/447.1, 447.3, 324
See application file for complete search history.

(56) References Cited

U.S. PATENT DOCUMENTS

| | | | | |
|---|---|---|---|---|
| 5,540,830 | A * | 7/1996 | Nishida et al. | 205/414 |
| 7,211,464 | B2 * | 5/2007 | Lieber et al. | 438/99 |
| 7,250,188 | B2 * | 7/2007 | Dodelet et al. | 427/115 |
| 7,338,590 | B1 * | 3/2008 | Shelnutt et al. | 205/628 |
| 7,399,703 | B2 * | 7/2008 | Kawakami | 438/669 |
| 7,504,132 | B2 * | 3/2009 | Afzali-Ardakani et al. | 427/256 |

OTHER PUBLICATIONS

Lu et al., "Structural evolution of [2+1] cycloaddition derivatives of single-wall carbon nanotubes: From open structure to closed three-membered ring structure with increasing tube diameter;" Journal of Molecular Structure, Theochem, 725: 255-257 (2005).
Kamaras et al., "Covalent bond formation to a carbon nanotube metal;" www.sciencemag.org, 1501, Science, 301:1501 (2003).
R.C. Haddon, "Pi-Electrons in Three Dimensions;" American Chemical Society, 21:243-249 (1988).
Niyogi et al., "Chemistry of single-walled carbon nanotubes;" American Chemical Society, 35:1105-1113 (2002).
Whitsitt et al., "LPD silica coating of individual single walled carbon nanotubes;" Journal of Materials Chemistry, 15:4678-4687 (2005).
Bauer et al., "Preparation of scratch and abrasion resistant polymeric nanocomposites by monomer grafting onto nanoparticles, FTIR and multi-nuclear NMR spectroscopy to the characterization of methacryl grafting;" Macromol. Chem. Phys. 201(18):2654-2659 (2000).
Chen et al., "Reactivity of the convex and concave surfaces of single-walled carbon nanotubes (SWCNTs) towards addition reactions: Dependence on the carbon-atom pyramidalization;" Chemphyschem. 1:93-97 (2003).
Chu et al., "Theoretical study of addition reactions of carbene, silylene, and germylene to carbon nanotubes;" Chemical Physics Letters, 394:231-237 (2004).
Colorado et al., "In-situ fabrication of freestanding single-walled carbon nanotube-silicate composite hex nuts;" Adv. Mater. 17:1634-1637 (2005).
Akasaka et al., "Photochemical bissilylation of C60 with Disilane;" J. Org. Chem. 64:566-569 (1999).
Lu et al., "The [2+1] cycloadditions of dichlorocarbene, silylene, germylene, and oxycarbonylnitrene onto the sidewall of armchair (5,5) single-wall carbon nanotube;" J. Phys. Chem. 107:8388-8391 (2003).
Duchet et al., "Influence of the deposition process on the structure of grafted alkylsilane layers;" Langmuir. 13:2271-2278 (1997).
Zhang et al., "The isomerization mechanism of X<ASWCNT (X-CH2 and SiH2);" Journal of Molecular Structure (Theochem), 681:225-230 (2004).
Velasco-Santos et al., "Chemical functionalization of carbon nanotubes through an organosilane;" Nanotechnology, 13:495-498 (2002).
Vast et al., "Chemical functionalization by a fluorinated trichlorosilane of multi-walled carbon nanotubes;" Nanotechnology, 15:781-785 (2004).
Fu et al., "Selective coating of single wall carbon nanotubes with thin SiO2 layer;" Nano Letters 2(4): 329-332 (2002).
Whitsitt et al., "Silica coated walled carbon nanotubes;" Nano Letters 3(6):775-778 (2003).
Hamon et al., "Effect of rehybridization on the electronic structure of single-walled carbon nanotubes;" J. Am. Chem. Soc. 123:11292-11293 (2001).

* cited by examiner

*Primary Examiner*—Timothy C Vanoy
*Assistant Examiner*—Michelle Hou
(74) *Attorney, Agent, or Firm*—Hoffman & Baron, LLP

(57) ABSTRACT

The invention provides adducts comprising a carbon nanotube with covalently attached silane moieties, and methods of making such adducts. Examples of silane moieties include trimethoxysilane; hexaphenyldisilane; silylphosphine; 1,1,1,3,5,5,5-heptamethyltrisiloxane; polydimethylsiloxane, poly (N-bromobenzene-1,3-disulfonamide); N,N,N',N'-tetrabromobenzene-1,3-disulfonamide; hexamethyldisilazane (HMDS); chlorotrimethylsilane (TMCS); trichloromethylsilane (TCMS); an alkyl(alkylamino)silane; a tri(alkoxy)silane; tert-butyldimethylsilane; monochloroaminosilane; dichloroaminosilane; trichloroaminosilane; and dimethylaminosilane.

20 Claims, 12 Drawing Sheets

Scheme 1. Representation of Typical Reactions between SWNTs and Appropriate Silane Precursors

Fig. 12

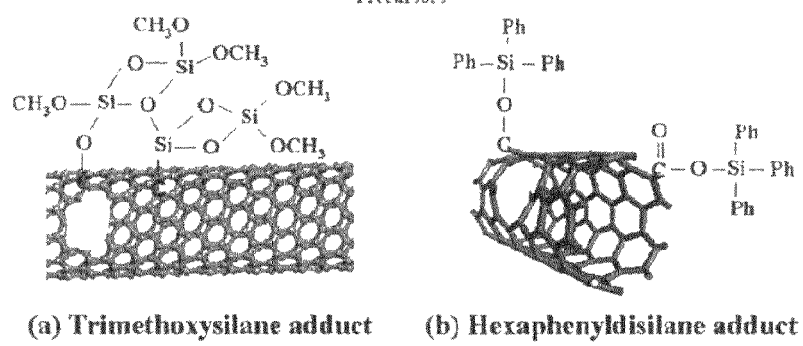

Scheme 2. Schematic Representation, Not Drawn to Scale, of the Carbon Nanotube Framework (CNT) with Attached Silane Precursors[a]

(a) Trimethoxysilane adduct   (b) Hexaphenyldisilane adduct

[a] (a) Trimethoxysilane adduct demonstrating dominance of Si—O—Si network along with the presence of —Si(OCH$_3$)$_n$ groups forming a coating (b) Hexaphenyldisilane adduct demonstrating attachment of —Si(Ph)$_3$ groups to oxygenated functionalities onto the ends and defect sites of the nanotube. Phenyl groups are represented by Ph.

1

SILYLATED CARBON NANOTUBES AND METHODS OF MAKING SAME

This application claims benefit from U.S. provisional Application Ser. No. 60/968,088, filed on Aug. 27, 2007, which application is incorporated herein by reference in its entirety.

This invention was made with government support under grant numbers DMR-0348239 and DMII-0403859 awarded by the National Science Foundation. The government has certain rights in the invention.

BACKGROUND OF THE INVENTION

Single-walled carbon nanotubes (SWNTs) possess unique structural, electronic, mechanical, and optical properties (Dresselhaus et al. *Carbon Nanotubes: Synthesis, Structure, Properties, and Applications*, Springer Verlag, Berlin, 2001; Falvo et al., *Nature* 1997, 389, 582). The combination of the helicity and diameter of SWNTs, defined by the roll-up vector, i.e. tube chirality, determines whether a tube is a metal or a semiconductor. One main advantage of understanding the electronic structure of carbon nanotubes is that as spatially constrained one-dimensional structures, they are the smallest dimensional systems that can be used for the efficient transport of electrons and optical excitations and hence are expected to be particularly important in the construction and integration of nanoscale devices.

The majority of electronics applications specifically require the isolation of semiconducting tubes (Bachtold et al., *Science* 2001, 294, 1317; Baughman et al., *Science* 2002, 297, 787; Wong et al., *Nature* 1998, 394, 52; Yang et al., *J. Phys. Chem. B* 2002, 106, 8994). However, the lack of control over the electronic properties of as-prepared nanotubes, e.g. the inability to reliably separate masses of semiconducting from metallic tubes, has created a major stumbling block for their incorporation into functional devices. Thus, there is an urgent need to obtain electronic monodispersity in nanotube samples. Generating such monodisperse samples of nanotubes should also allow for detailed studies of diameter and chirality dependence of many different structural properties that are of fundamental interest in low-dimensional science.

One solution to this problem involves the controllable use of covalent chemistry to modify the sidewall surfaces of tubes to enhance the relative populations of either metallic or semiconducting tubes. Some of these types of functionalization reactions, such as osmylation and diazotisation, involve extraction of electrons from the nanotube itself (Bahr et al., *J. Am. Chem. Soc.* 2001, 123, 6536; Banerjee et al., *J. Am. Chem. Soc.* 2004, 126, 2073; Dyke et al., *Nano Lett.* 2003, 3, 1215). In particular, with these reactions, metallic SWNTs, due to their finite and readily available electron density at the Fermi level, are better able to stabilize the transition state involved, will consequently accelerate the forward rate of reaction, and hence will preferentially react as compared with semiconducting tubes. Another means of altering the relative distribution of metallic vs. semiconducting carbon nanotubes involves the chemical derivatization of nanotubes with a high K dielectric coating material, such as Si-containing species.

Prior work on coating SWNTs with $SiO_2$ and analogous derivatives has focused on a number of methods. An early study reported on the use of a promoter layer, 3-aminopropyltriethoxysilane, followed by a modified Stöber reaction to generate silica (Fu et al., *Nano Lett.* 2002, 2, 329). Peptides have been used to both suspend SWNTs as well as direct the precipitation of silica onto their surfaces (Pender et al., *Polymer Preprints (American Chemical Society; Division of Polymer Chemistry)* 2005, 46, 83). Treatment of a dispersion of SWNTs in an aqueous surfactant solution with an acidic solution of fumed silica resulted in silica-coated SWNTs (Whitsitt et al., *J. Mater. Chem.* 2005, 15, 4678), whereas a complementary method for generating silica-coated SWNTs was devised using a basic solution of aqueous sodium silicate (Colorado et al., *Adv. Mater.* 2005, 17, 1634). Finally, the same group coated SWNTs with fluorine-doped silica by liquid phase deposition using a $silica/H_2SiF_6$ solution in the presence of surfactant.

Theoretical studies (Lu et al., *J. Phys. Chem. B* 2003, 107, 8388; Chu et al., *Chem. Phys. Lett.* 2004, 394, 231) have postulated that the [2+1]cycloaddition of silylene on nanotube sidewalls is site-selective, occurring preferentially on the 1,2-pair site and favoring opened structures (Zhang et al., *J. Molec. Struct. (Theochem)* 2004, 681, 225; Lu et al., *J. Molec. Struct. (Theochem)* 2005, 725, 255). Organosilanes have been extensively used as coupling agents on hydroxylated surfaces for generating organic coatings, with the idea that the electrical properties of carbon nanotubes can be appropriately adjusted through rational chemical functionalization (Duchet et al., *Langmuir* 1997, 13, 2271). In previous work, the silylation of oxidized multi-walled carbon nanotubes has been performed with a variety of reagents including tert-butylchlorodimethylsilane and 1-(tert-butyldimethylsilyl)imidazole (Velasco-Santos et al., *Nanotechnology* 2002, 13, 495; Vast et al., *Nanotechnology* 2004, 15, 781).

However, prior art attempts at silylation of nanotubes have many disadvantages. For example, prior art attempts at silylation of nanotubes spatially limited silylation to defect sites and ends. Moreover, prior silylation techniques required harsh oxidative methods.

SUMMARY OF THE INVENTION

In one embodiment, the present invention are adducts comprising a carbon nanotube with covalently attached silane moieties. Examples of silane moieties include trimethoxysilane; hexaphenyldisilane; silylphosphine; 1,1,1,3,5,5,5-heptamethyltrisiloxane; polydimethylsiloxane, poly(N-bromobenzene-1,3-disulfonamide); N,N,N',N'-tetrabromobenzene-1,3-disulfonamide; hexamethyldisilazane (HMDS); chlorotrimethylsilane (TMCS); trichloromethylsilane (TCMS); an alkyl(alkylamino)silane; a tri(alkoxy)silane; R1SiHR2R3, wherein R1-R3 is a substituted or unsubstituted hydrocarbyl with 1-10 carbon atoms; tert-butyldimethylsilane; monochloroaminosilane; dichloroaminosilane; trichloroaminosilane; and dimethylaminosilane. Preferably, the adduct comprises covalently attached trimethoxysilane (TM) moieties or covalently attached hexaphenyldisilane (HPD) moieties.

About 3% to 30% of the sidewall carbon atoms of the nanotube of the adducts have a silane moiety attached. Preferably, the range of the quantity of sidewall carbon atoms of the nanotube that have a silane moiety attached has a lower boundary of approximately 3%, 5%, 8%, 10% or 12%. Preferably, the range of the quantity of sidewall carbon atoms that have a silane moiety attached has an upper boundary of approximately 30%, 25%, 20% or 16%.

The nanotube of the adducts can be a SWNT or a MWNT, e.g., DWNT. The nanotube of the adducts can be semiconducting or metallic.

Preferably, the diameter of the adduct is from about 70% to about 85% larger than the diameter of a SWNT. For example, the diameter of the adduct with TM moieties is from about 70% to about 80% larger than the diameter of a SWNT. Also, for example, the diameter of the adduct with HPD moieties is from about 75% to about 85% larger than the diameter of a SWNT.

In one embodiment, the adducts have a high degree of solubility in organic or aqueous solvents. Examples of organic solvents include dimethylsulfoxide (DMSO), tetrahydrofuran (THF), dimethylformamide (DMF), methanol, ethanol, 2-propanol, acetone, o-dichlorobenzene (ODCB), dimethylsulfoxide (DMSO), tetrahydrofuran (THF), ethyl acetate, diethyl ether, hexanes, alkanes and benzene.

For example, an adduct with TM moieties has a solubility of about 1 mg/mL in dimethylformamide. Also, for example, an adduct with HPD moieties has a solubility of almost about 0.4 mg/mL in dimethylformamide In another embodiment, the invention is a method of functionalizing a plurality of carbon nanotubes with silane moieties. The method comprises contacting a carbon nanotube dispersion with a silane moiety to form a precursor mixture, and irradiating the precursor mixture to functionalize the nanotubes with silane moieties. Examples of silane moieties are described above.

In one embodiment, the method further comprises isolating functionalized adducts. In one embodiment, the method further comprises flushing the carbon nanotube dispersion with argon and/or contacting the carbon nanotube dispersion with extra dry 2-propanol before exposure to the silane moiety and/or any catalyst.

In a preferred embodiment, the silane moiety is trimethoxysilane and the carbon nanotube dispersion is further contacted with a transitional metal catalyst to form the precursor mixture. Examples of transitional metal catalysts include a platinum catalyst, a rhodium catalyst, a Ruthenium catalyst, a gold catalyst, a cobalt catalyst and nickel catalyst.

Examples of platinum catalysts include hexachloroplatinate (IV) hexahydrate, hydrogen hexachloroplatinate (IV) hexahydrate catalyst, Speier's catalyst, PtCl[2](PEt[3])[2], Pt(PPh[3])[2](C[2]H[4]), Pt(PPh[3])[4], Pt[ViMeSiO][4], Pt/C, $(C_2H_4)Pt(PPh_3)_2$, $PtCl_2$, Pt/SAPO-11, $Pt/Al_2O_3$, $TpMe_2PtMe_2H$ and Karstedt's catalyst (Pt-divinyltetramethyldisiloxane). Further examples of catalysts include Ni(PEt3) 4, ([AuCl(PPh$_3$)]) and Rh(PPh$_3$)$_3$I. Preferably, the carbon nanotube dispersion is exposed to the catalyst before being exposed to trimethoxysilane.

Typically, the amount by weight of the nanotube dispersion to the amount by weight of the TM is from about 1:1 to about 1:50. Also typically, the amount by weight of the nanotube dispersion to the amount by weight of the TM is from about 1:1 to about 1:10.

In a preferred embodiment, the silane moiety is hexaphenyldisilane (HPD). Typically, the amount by weight of the nanotube dispersion to the amount by weight of the HPD is from about 1:1 to about 1:50. Also typically, the amount by weight of the nanotube dispersion to the amount by weight of the HPD is from about 1:1 to about 1:10.

In a further embodiment, the invention is a method of providing semiconducting single SWNTs with a diameter of less than a selected diameter, e.g., less than about 1.5 nanometer. The method comprises contacting a carbon nanotube dispersion with a silane moiety to form a precursor mixture; irradiating the precursor mixture whereby SWNTs with a diameter of less than about 1.5 nanometer are functionalized with silane moieties; and precipitating the SWNTs functionalized with silane moieties from the mixture, wherein single SWNTs with a diameter of less than about 1.5 nanometer are provided. Examples of other selected diameters include less than 1.4 nm, less than one nm, less than about 0.85 nm, less than about 0.75 nm, less than about 0.65 nm, and less than about 0.55 nm. Preferably, the silane moiety is HPD.

In another embodiment, the invention is a method of providing semiconducting single SWNTs with a diameter of less than a selected diameter, e.g., less than about 1.4 nanometer. The method comprises contacting a carbon nanotube dispersion with a transitional metal catalyst and silane moiety to form a precursor mixture; irradiating the precursor mixture whereby SWNTs with a diameter of less than about 1.4 nanometer are functionalized with silane moieties; and precipitating the SWNTs functionalized with silane moieties from the mixture, wherein single SWNTs with a diameter of less than about 1.4 nanometer are provided. Examples of other selected diameters include less than one nm, less than about 0.85 nm, less than about 0.75 nm, less than about 0.65 nm, and less than about 0.55 nm. Preferably, the silane moiety is trimethoxysilane (TM).

The present invention overcomes the disadvantages of the prior art. The present invention involves the silylation of pristine, unoxidized SWNTs. The silylation reaction is not spatially limited to defect sites and ends. Moreover, the silylation protocol does not require harsh oxidative methods.

BRIEF DESCRIPTION OF DRAWINGS

FIG. 12, Scheme 2. A schematic representation, not drawn to scale, of the carbon nanotube framework (CNT) with attached silane precursors. (a) Trimethoxysilane adduct demonstrating dominance of Si—O—Si network along with the presence of —Si(OCH$_3$) groups forming a coating. (b) Hexaphenyldisilane adduct demonstrating attachment of —Si(Ph)$_3$ groups to oxygenated functionalities onto the ends and defect sites of the nanotube. Phenyl groups are represented by Ph.

DETAILED DESCRIPTION OF THE INVENTION

Figure 1:
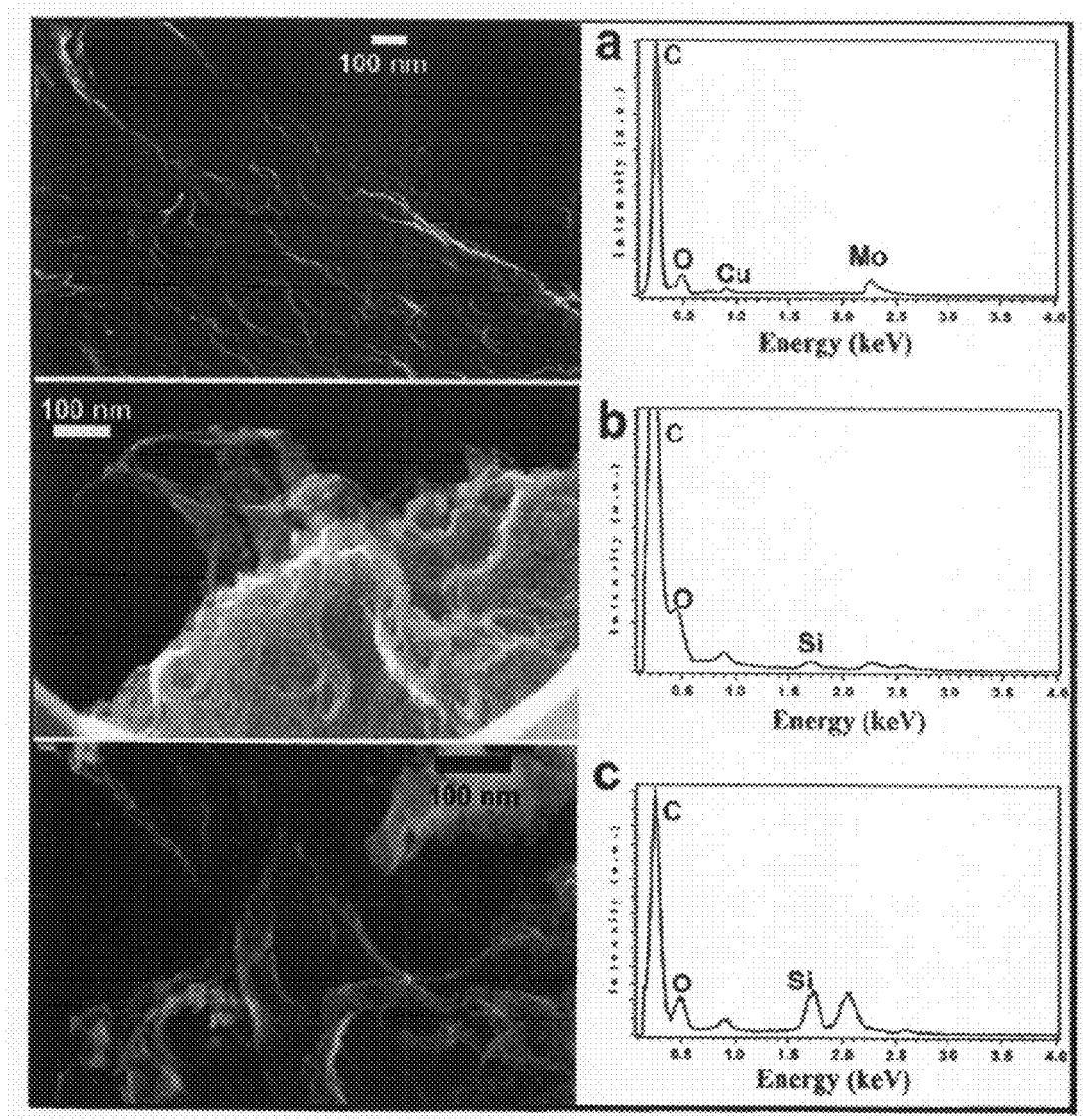
FIG. 1. SEM images and EDS data for (a) SWNT starting material; (b) hexaphenyldisilane-SWNT adducts; (c) trimethoxysilane-SWNT adducts. Copper signal originates from the sample grid and the molybdenum signal arises from the catalyst used to synthesize the nanotube.

The present invention provides silylated carbon nanotube adducts and methods of making such adducts.

Adducts

An adduct of the present invention comprises a carbon nanotube with covalently attached silane moieties, i.e., a silylated nanotube.

The carbon nanotubes of the adducts comprise graphene in cylindrical form. The nanotubes preferably have open ends. Alternatively, the nanotubes can have one or two hemispherical caps on their ends. In addition to the hexagonal carbon rings of graphene, the caps can comprise pentagonal rings of carbon. The carbon nanotube can be a semi-conducting nanotube or a metallic nanotube. (A metallic nanotube has no band gap.)

The carbon nanotube can be either a single-walled nanotube (SWNT) or a multi-walled nanotube (MWNT). A SWNT comprises only one nanotube. A MWNT comprises more than one nanotube each having a different diameter. Thus, the smallest diameter tube is encapsulated by a larger diameter tube, which in turn, is encapsulated by another larger diameter nanotube. A MWNT comprises, for example, up to about fifty nanotube shells. Preferably, the MWNT nanotube is a double-walled nanotube (DWNT).

SWNTs typically have a diameter of about 0.7 to about 2.5 nm, and a length of up to about one mm. MWNTs typically have a diameter of about 3 to about 30 nm, and a length of up to about one mm.

SWNTs and MWNTs are produced, typically, as bundles. A bundle comprises a plurality of SWNTs or MWNTs. The diameter of a bundle of SWNTs is typically about 10 to 20 nm. The diameter of a bundle of MWNTs is typically about 2.5 to 250 nm.

The carbon nanotubes can be prepared by methods known in the art. For example, carbon nanotubes can be prepared by the laser vaporization. (Thess et al. *Science* 273: 483 (1996)). Also, carbon nanotubes can be prepared by arc discharge (Ishigami et al., *Chem. Phys. Lett.* 319:457 (2000); Su et al., *Chem. Phys. Lett.* 322:321 (2000); Journet et al., *Nature* 388:756 (1997); Colbert et al. *Science* 266:1218, (1994)); Shi et al., *Carbon* 37:1449 (1999); and Ebbeson et al., *Nature* 358:220 (1992)). The carbon nanotubes can be prepared by catalytic chemical vapor deposition (Kukovitsky, E. F. et al. *Chem. Phys. Lett.* 317:65 (2000); Su, M. et al. *Chem. Phys. Lett.* 322:321 (2000); Li et al. *Science* 274:1701 (1996); and Pan, Z. et al. *Chem. Phys. Lett.* 299:97 (1999)).

The carbon nanotubes may optionally be doped with other elements, for example, with metals, such as boron or nitrogen; or gases, such as ammonia, nitrogen and oxygen, by methods known in the art.

For the purposes of this specification, a "silane moiety" is any moiety that contains silane, for example, a hydrocarbon containing silane.

Examples of silane moieties suitable for the present invention include trimethoxysilane (TM); hexaphenyldisilane (HPD); a silylphosphine; 1,1,1,3,5,5,5-heptamethyltrisiloxane; polydimethylsiloxane, poly(N-bromobenzene-1,3-disulfonamide); N,N,N',N'-tetrabromobenzene-1,3-disulfonamide; hexamethyldisilazane (HMDS); chlorotrimethylsilane (TMCS); trichloromethylsilane (TCMS); an alkyl(alkylamino)silane; a tri(alkoxy)silane (i.e., (RO)$_3$SiH wherein R=Me and/or Et); R1SiHR2R3 wherein R1-R3=C1-10 (un)substituted hydrocarbyl; tert-butyldimethylsilane; monochloroaminosilane; dichloroaminosilane; trichloroaminosilane; and dimethylaminosilane.

Throughout this specification, there are ranges defined by upper and lower boundaries. Each lower boundary can be combined with each upper boundary to define a range. The lower and upper boundaries should each be taken as a separate element.

In one embodiment of the present invention, adducts are provided in which silane moieties are attached to the sidewalls of the nanotube. The quantity of silane moieties that are attached to the sidewall of a carbon nanotube can be expressed by defining the percentage of carbon atoms which have a silane moiety attached. The percentage can be expressed as a percentage range. Preferably, the range of the quantity of sidewall carbon atoms that have a silane moiety attached has a lower boundary of approximately 3%. Examples of other lower boundaries include approximately 5%, 8%, 10% and 12%. Preferably, the range of the quantity of sidewall carbon atoms that have a silane moiety attached has an upper boundary of approximately 30%. Examples of other upper boundaries include approximately 16%, 20% and 25%. An example of a range is about 5 to 20%.

For example, in one embodiment, the invention provides a carbon nanotube with covalently attached trimethoxysilane (TM) moieties wherein up to about 30% of the sidewall carbon atoms of the nanotube have a TM moiety attached. In another embodiment, the invention provides a carbon nanotube with covalently attached hexaphenyldisilane (HPD) moieties wherein up to about 10% of the sidewall carbon atoms of the nanotube have a HPD moiety attached.

In a preferred embodiment, the silane moieties form a continuous, homogeneous coating, which is effectively uniform in height along the length of the nanotube. The thickness of the coating is such that the diameter of the adduct is from about 10% to about 90% larger than the diameter of the nanotube before being coated. The thickness achieved is dependent on the reaction conditions, as discussed below, and on the specific silane moiety used.

For example, the thickness of a coating comprising trimethoxysilane moieties is such that the diameter of the adduct can be from about 10% to about 90% larger than the diameter of the SWNT before being coated. As an additional example, the thickness of a coating comprising hexaphenyldisilane moieties is such that the diameter of the adduct can be from about 75% to about 85% larger than the diameter of the SWNT before being coated.

In a preferred embodiment, the adducts of the present invention have a high degree of solubility in organic or aqueous solvents. For example, the adducts have a high degree of solubility in, for example, dimethylsulfoxide (DMSO), tetrahydrofuran (THF), dimethylformamide (DMF), methanol, ethanol, 2-propanol, acetone, o-dichlorobenzene (ODCB), dimethylsulfoxide (DMSO), tetrahydrofuran (THF), ethyl acetate, diethyl ether, hexanes, alkanes and benzene.

For example, certain trimethoxysilane-SWNT adducts have a solubility of about 1 mg/mL in DMF. As a further example, certain hexaphenyldisilane-SWNT adducts have a solubility of up to about 0.4 mg/mL in DMF.

Methods of Making the Adducts

In another aspect, the present invention provides methods of functionalizing a plurality of carbon nanotubes with silane moieties. The method comprises contacting a carbon nanotube dispersion with silane moieties to form a precursor mixture. The amount by weight of the nanotube dispersion to the amount by weight of the silane moieties is preferably from about 1:1 to about 1:100; from about 1:1 to about 1:50; or about 1:1 to about 1:10. The precursor mixture is then irradiated to functionalize the nanotubes with silane moieties. Preferably, irradiation takes place at ambient temperature.

Examples of preferred silane moieties are described above. Depending upon the moiety used, in some embodiments, a catalyst is preferably included in the nanotube dispersion along with the silane moieties.

Preferably, the catalyst is a transitional metal catalyst. Some examples of suitable transitional metal catalysts include platinum catalysts, rhodium catalysts, ruthenium catalysts, gold catalysts, cobalt catalysts and nickel catalysts.

Some examples of suitable platinum catalysts include hexachloroplatinate (IV) hexahydrate, Speier's catalyst, PtCl[2](PEt[3]) [2], Pt(PPh[3])[2](C[2]H[4]), Pt(PPh[3])[4], Pt[ViMeSiO][4], Pt/C, $(C_2H_4)Pt(PPh_3)_2$, $PtCl_2$, Pt/SAPO-11, $Pt/Al_2O_3$, $TpMe_2PtMe_2H$ or Karstedt's catalyst (Pt-divinyltetramethyldisiloxane).

Examples of other suitable catalysts include $Ni(PEt_3)_4$, $([AuCl(PPh_3)])$ and $Rh(PPh_3)_3I$.

In the embodiment wherein trimethoxysilane is used as the silane moiety, it is preferred that a platinum catalyst is used, e.g., hydrogen hexachloroplatinate (IV) hexahydrate. The carbon nanotube dispersion can be exposed to the catalyst before being exposed to trimethoxysilane; or the carbon nanotube dispersion can be exposed to the catalyst simultaneously with trimethoxysilane.

Preferably, the silylation reaction is performed in the absence of water. Accordingly, preferably, the method further comprises flushing the carbon nanotube dispersion with argon and/or contacting the carbon nanotube dispersion with extra dry 2-propanol before exposure to the silane moiety and/or any catalyst.

The whole dispersion, or a portion of the dispersion, is irradiated with ultraviolet light at room temperature. Preferably, the wavelength of the ultraviolet light is between approximately 200 and 350 nm. An example of a suitable wavelength is 254 nm. Preferably, wavelengths other than the selected wavelength are blocked out. For example, a bandpass filter can be used at 254 nm to block out other wavelengths. Preferably, mixtures are stirred during irradiation.

| Near | NUV | 400 nm-200 nm |
|---|---|---|
| UVA, long wave, or black light | | 400 nm-320 nm |
| UVB or medium wave | | 320 nm-280 nm |
| UVC, short wave, or germicidal | | Below 280 nm |
| Far or vacuum | FUV, VUV | 200 nm-10 nm |
| Extreme or deep | EUV, XUV | 31 nm-1 nm |

Ultraviolet irradiation allows for silylation of the nanotube surfaces, i.e., the coating of nanotubes with silane moieties. The time of irradiation correlates with the density of the coating. That is, as the time of irradiation is increased, the denser the coating becomes, provided that a sufficient amount of silane moieties is supplied.

Accordingly, the time for irradiation is adjusted depending upon the density of the coating desired and the size of the nanotube dispersion. For example, irradiation can last for at least about 1 hour, about 6 hours, about 12 hours, about 24 hours, about 36 hours, about 48 hours, or about 60 hours. There is no necessary maximum amount of time for irradiation. Irradiation can last until silane moieties thoroughly cover the nanotubes.

Methods of Selective Silylation of Nanotubes

In one aspect of the present invention, a method of providing single carbon nanotubes, or nanotube bundles, with less than a selected diameter is provided. For example, single SWNTs with a diameter of less than 1.5 nm, less than 1.4 nm, or less than one nm is provided.

In particular, by adjusting the reaction conditions, certain diameters of the nanotubes are preferentially silylated. Smaller diameter nanotubes, because of increased strain, are more susceptible to silylation. Thus, to favor silylation of smaller diameter nanotubes, either a limited amount of silane moieties is provided and/or the period of irradiation is in the shorter end of the range and/or the intensity of the irradiation is at a lower level.

For example, irradiation can take place for as little as about twelve hours to about twenty-four hours (adjusting for the size of the dispersion, as would be known by a skilled artisan). Alternatively, instead of shortening the period of irradiation, the intensity of the light can be reduced.

For the purposes of this specification, typically, a small diameter nanotube is a nanotube that has a diameter of less than about 1.5 nm; more typically, less than about 1.0 nm; most typically, less than about 0.6 nm; and optimally, less than about 0.5 nm.

For example, when using TM moiety, if the reaction time is 48 hours, then nanotubes of less than 1.0 nm are preferentially silylated; whereas, if the reaction time is 24 hours, then nanotubes of less than 0.5 nm are preferentially silylated (at a fixed level of irradiation).

In some embodiments, the smaller diameter nanotubes are separated from the mixture. There is an inverse correlation between the diameter of a nanotube and the percentage of the nanotube's surface which is silylated, i.e., the smaller the diameter of a nanotube, the greater proportion of its surface area which is silylated. Without wishing to be bound by a theory, it is believed that the degree of silylation correlates with solubility and thus, the more functionalized (smaller diameter) tubes would be more easily solubilized. The more easily solubilized nanotubes are readily recovered by solvent removal, while the less functionalized tubes would be left behind, to be recovered by filtration.

Alternatively, the size of the adducts are used to separate the smaller diameter nanotubes from the mixture. For example, size exclusion chromatography can be used to retrieve different size nanotubes. Additionally, since silylated nanotubes are denser than uncoated nanotubes, separation can be based on density. For example, the silylated dispersion can be centrifuged, whereby the denser silylated nanotubes are pulled in the direction of the centrifugal force.

In another aspect of the invention, a method of differentiating between metallic nanotubes and semiconducting nanotubes is provided. Certain silane moieties, e.g., TM moieties, preferentially silylate semi-conducting nanotubes vis-à-vis metallic tubes. To favor silylation of semi-conducting nanotubes, silylation is carried out with the reaction conditions described above for preferential silylation of smaller diameter tubes.

Figure 11:
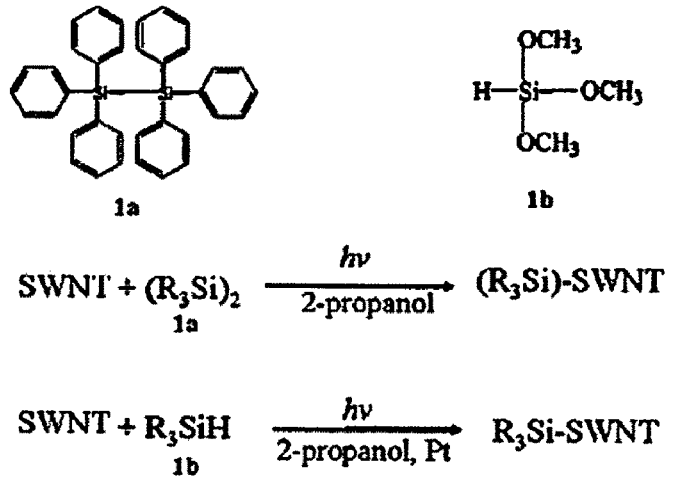
FIG. 11. Scheme 1. Representation of typical reactions between SWNTs and appropriate silane precursors.

While not wanting to be bound by a theory, it is hypothesized that the mechanism of the silylation reaction with SWNTs is similar to that of fullerenes, as shown in Scheme 1 (FIG. 11) (Akasaka et al., *J. Org. Chem.* 1999, 64, 566). However, the chemical reactivity of these two carbonaceous systems likely differs. That is, whereas in fullerenes, the relief of the pyramidalization strain energy results in addition reactions being energetically favorable, in the case of SWNTs, $\pi$-orbital misalignment is expected to have a greater influence (R. C. Haddon, *Acc. Chem. Res.* 1988, 21, 243). This misalignment, associated with bonds at an angle to the tube circumference, is the origin of torsional strain in nanotubes, and relief of this strain controls the extent to which addition reactions occur with nanotubes. Moreover, it is expected that smaller-diameter tubes would be more reactive than larger-diameter tubes since n-orbital misalignment as well as pyramidalization scale inversely with tube diameter (Niyogi et al., *Acc. Chem. Res.* 2002, 35, 1105; Hamon et al., *J. Am. Chem. Soc.* 2001, 123, 11292; Chen et al., *Chem. Phys. Chem.* 2003, 4, 93).

Thus, in one embodiment, the present invention provides silylation of raw, pristine single-walled carbon nanotubes. Specifically, commercially available CoMoCAT (Co/Mo catalyst developed by Southwest Nanotechnologies in Oklahoma, U.S.) SWNTs were sidewall-functionalized (a) with trimethoxysilane and in a separate experiment, (b) with hexaphenyldisilane. Raman analyses demonstrated selective reactivity of smaller-diameter semiconducting nanotubes. Fourier transform infrared (FT-IR) spectroscopy, nuclear magnetic resonance ($^{29}$Si NMR) spectroscopy, X-ray photoelectron spectroscopy (XPS), and energy dispersive X-ray spectroscopy (EDS) data provided evidence for chemical attachment of organosilanes onto the carbon nanotube surface. UV-visible data also yielded evidence for selectivity and functionalization.

In addition, several microscopy techniques, including atomic force microscopy (AFM), high-resolution transmission electron microscopy (HRTEM), and scanning electron microscopy (SEM), were used to determine the degree of nanotube purity and functionalization. Most importantly, these structural characterization techniques confirmed that silylation does not result in any noticeable form of destruction to the nanotube surface. Moreover, it was noted, upon silylation, that the solubility and stability of the SWNTs increased dramatically in DMF as compared with pristine, unfunctionalized CoMoCat nanotubes.

EXAMPLES

Pre-treatment of SWNTs. In order to ensure that the starting material, namely the unreacted SWNTs, were free of silicon, a known purification method was used to initially treat the tubes (Alvarez et al., Chem. *Matter.* 2002, 14, 1853). Specifically, a sample of nanotubes was suspended in a 0.2 M NaOH solution, while stirring for 24 h at 65° C. Upon filtration through a polycarbonate 0.2 µm membrane, the remaining solid was washed with deionized water until the pH was neutral. The sample was subsequently allowed to dry overnight in a desiccator (Herrera et al., *J. Nanosci. Nanotech.* 2003, 3, 133). SEM, TEM, and HRTEM images as well as EDS data (FIGS. 1 and 2) confirm that the starting material was free from any form of silicon. These samples are herein referred to as "SWNT starting materials."

Control Experiment. In order to better understand the effect of only UV irradiation on the tube surface, a sample of base-treated SWNTs was placed in 2-propanol and was allowed to stir for 48 h with exposure to the UV lamp. HRTEM data (FIG. 2) confirm that there was no visible damage occurring on tube sidewalls. In addition, Raman data taken on this sample were compared with that obtained on silane adducts. The results confirm that observed changes in the Raman data were likely due to the functionalization reaction as opposed to any process associated with lamp irradiation. These samples are herein referred to as "controls."

Silylation of SWNTs. Into a rectangular quartz holder, the interior of which was filled with argon, was placed ~40 mg of dried SWNTs in the presence of extra dry 2-propanol (Aldrich). The whole setup was sealed within a Schlenk setup to avoid the presence of moisture. The tubes were gently dispersed by sonication for a few seconds after which vigorous stirring was performed.

(a) For the reaction with hexaphenyldisilane, 50 mg of the silane precursor was inserted into a Schlenk flask (flushed with argon) to which 20 ml of extra dry 2-propanol was then added. Upon dissolution, this solution was then combined with the SWNT dispersion. Although it may not have been completely necessary for the hexaphenyldisilane reaction to have been performed in the absence of water, as in the case with fullerenes, the above precautions were taken to ensure a more controlled environment (Akasaka et al., *J. Org. Chem.* 1999, 64, 566). Irradiation of the mixture with a 500 W mercury xenon lamp for 48 h was subsequently performed. The functionalized adduct was isolated by filtering the mixture over a 0.2 µm polycarbonate membrane, after which the remaining solid was washed several times with 2-propanol and distilled water to remove any unreacted organosilane precursor.

(b) In the case of trimethoxysilane, use of a hydrogen hexachloroplatinate (IV) hexahydrate (38-40% Pt) catalyst was the main modification in a reaction protocol similar to that reported for hexaphenyldisilane. In this case, the catalyst solution was initially added to a stirred solution of SWNTs, after which the organosilane precursor (trimethoxysilane, 0.016 mol) was inserted. The entire process was performed under Schlenk conditions to ensure the absence of moisture in the system. After irradiation for 48 h, filtration followed by washing and drying was performed to isolate the functionalized adduct.

Solubility. Solubility tests were performed in DMF. The trimethoxysilane-SWNT adduct was found to maintain a solubility value of ~1 mg/ml whereas the hexaphenyldisilane-SWNT adduct, pristine CoMoCat SWNTs, and control materials all showed solubilities less than 0.4 mg/ml. Most importantly, solutions of trimethoxysilane-SWNT adducts remained stable for more than seven months, whereas solutions of all of the other samples precipitated within hours. Images of solutions and dispersions of all of these samples are available at http://pubs.acs.org.

Spectroscopy. FTIR data were obtained on a Nexus 670 (Thermo Nicolet) equipped with a single reflectance ZnSe ATR accessory in addition to a KBr beam splitter and a DTGS KBr detector for mid-IR as well as a $CaF_2$ beam splitter and an InGaAs detector for near-IR. Powder samples were placed onto a ZnSe crystal where data were taken with a reproducible pressure. Background corrections with the ZnSe crystal were performed in both ranges.

UV-visible spectra were collected on a Thermospectronics UV1 instrument using quartz cells possessing a 10 mm path length at a resolution of 1 nm. Samples were sonicated in DMF for 10-30 min and were subsequently centrifuged. Pristine CoMoCat samples were sonicated for the longer time periods to ensure solubility. The supernatant decants were collected and diluted to approximately the same absorption intensity, for comparative purposes, at a wavelength of 900 nm prior to spectral acquisition.

Raman spectra were obtained on solid samples dispersed in ethanol and placed onto a Si wafer. Spectra were obtained on a Renishaw 1000 Raman microspectrometer with excitation from argon ion (514.5 nm), He—Ne (632.8 nm), and diode (780 nm) lasers, respectively. In addition, a Renishaw System 1000 microscope with a tunable argon ion laser was used to acquire Raman data at 488 nm excitation. A 50× objective and low laser power density were used for the irradiation of the sample and for signal collection. The laser power was kept sufficiently low to avoid heating of the samples by optical filtering and/or defocusing of the laser beam at the sample surface. Spectra were collected in the range of 3000-100 $cm^{-1}$ with a resolution of 1 $cm^{-1}$.

$^{29}Si$ NMR spectra were recorded at room temperature on a Bruker Solid State

Spectrometer operating at 149.05 MHz for $^{29}Si$. A typical $^{29}Si$ path length of 5 μs was used and varying numbers of scans (depending on the sample involved) were performed. Powdered samples were placed in 4 mm rotor sample holders.

In collecting the XPS data, pressed wafers of the samples were attached to a stainless steel holder using conductive double-sided carbon tape which was then installed in the vacuum chamber of a Model DS800 XPS surface analysis system manufactured by Kratos Analytical Plc (Manchester, UK). The chamber was evacuated to a base pressure of ~5×10$^{-9}$ torr. A hemispherical energy analyzer was used for electron detection. XPS spectra were collected using a Mg K-alpha X-ray source, at an 80 eV pass energy, and in 0.75 eV steps for each sample survey spectrum. Collected spectra were plotted and used to generate estimates of the atomic and weight concentrations of the elements, as indicated by peaks present in the spectral data (available as SI at http://pubs.acs.org). High-resolution spectra were collected for the major elements detected in order to study relevant chemical bonding structures. These data were obtained at a pass energy of 40 eV and in 0.1 eV steps. High-resolution data were subsequently peak-fitted, plotted and tabulated in order to illustrate the chemical species present for each major element detected (available as SI at http://pubs.acs.org).

Microscopy. HRTEM images, as well as EDS data, were obtained on a JEOL 2010F HRTEM, equipped with an Oxford INCA EDS system, at an accelerating voltage of 200 kV. Samples were prepared by drying sample droplets from an ethanolic dispersion onto a 300-mesh Cu grid coated with a lacey carbon film. Prior to deposition, this dispersion was briefly sonicated for 10 s to ensure a uniform, homogeneous concentration of the carbon nanotubes within the solution.

Samples for SEM were studied using a field-emission SEM (FE-SEM Leo 1550 with EDS capabilities), operating at accelerating voltages of 2-10 kV at a 2 mm working distance. In fact, these samples were drop dried onto 300 mesh Cu grids and held over a Be plate inside a homemade sample holder.

AFM height images were acquired in Tapping Mode in air at resonant frequencies of 50-75 kHz with oscillating amplitudes of 10 to 100 nm. The samples were dispersed in DMF, spin coated onto a freshly cleaved HOPG substrate, and finally imaged with Si tips (force modulation etched silicon probes, Nanoworld (k=3-6 N/m)) using a Multimode Nanoscope IIIa (Digital Instruments, Santa Barbara, Calif.).

Results

Electron Microscopy. SEM images of SWNT starting materials, trimethoxysilane-SWNT adducts, and hexaphenyldisilane-SWNT adducts are shown in FIG. 1, along with their respective EDS data. It is evident that the initial starting material, consisting of a dense 'spaghetti' mat of nanotubes, was indeed very pure and relatively free from amorphous carbon and silica impurities. The absence of silica impurities in the starting material was also confirmed by XPS and EDS analyses performed on these samples. Bundles of single-walled carbon nanotubes were observed, ranging in size from ~4-20 nm in diameter, in addition to the presence of individual tubes of ~1 nm diameter. It is evident from the images obtained for both types of functionalized adducts, FIGS. 1 *b* and *c*, that a layer of coating formed on the surfaces of bundles of these tubes as well as on those of single tubes. From EDS data, the presence of silica was noted on these derivatized adducts, hypothesized to have originated from the presence of attached organosilane precursors.

Figure 2:
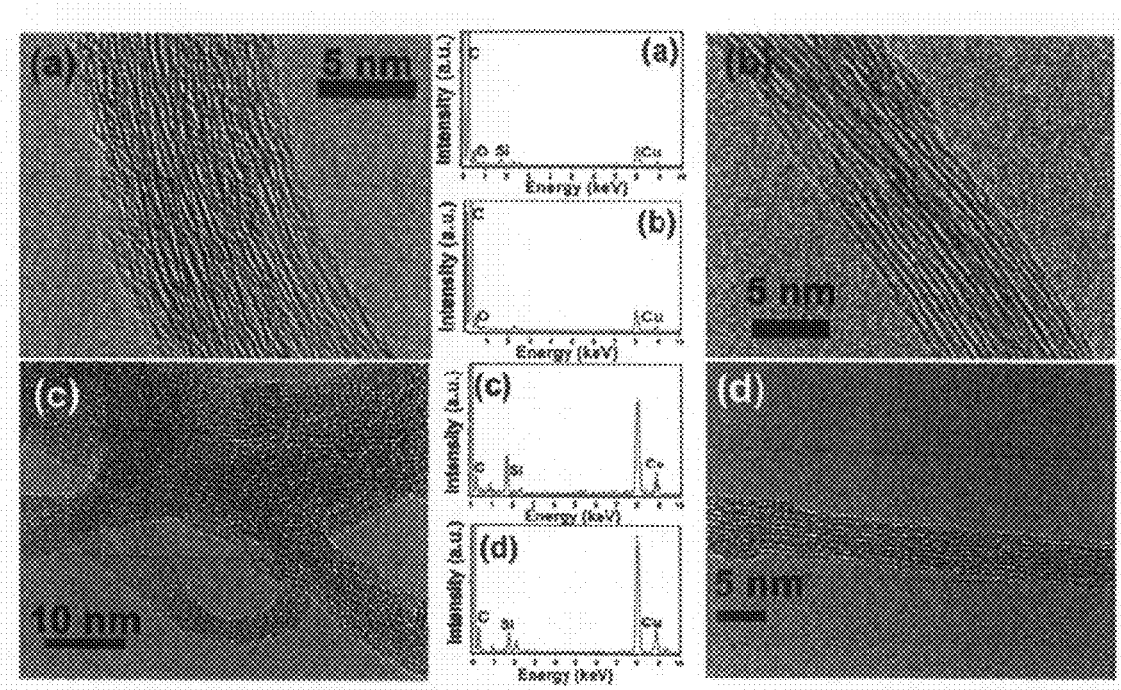
FIG. 2. HRTEM and EDS data for (a) pristine CoMoCat SWNT starting materials; (b) control samples; (c) hexaphenyldisilane-SWNT adducts; and (d) trimethoxysilane-SWNT adducts.

It is also apparent from collected SEM images that the nanotubes retained their structural features and were not obviously damaged by the silylation process itself. This assertion was also further confirmed by HRTEM. FIG. 2 shows images of pristine CoMoCat SWNTs, of controls, and of the two functionalized adducts, respectively. From the EDS analysis, the starting material of this particular reaction, namely base-treated nanotubes, was effectively free of any form of silicon. After the reaction (FIGS. 2*c* and *d*), it is clear that silicon was in fact present on localized areas of the tubes in the form of a coating on the nanotube surface. Moreover, it should be noted that the tubes were neither damaged by the base treatment nor by UV lamp irradiation, as shown in the control experiment data as well as in the functionalized nanotube results.

Figure 3:
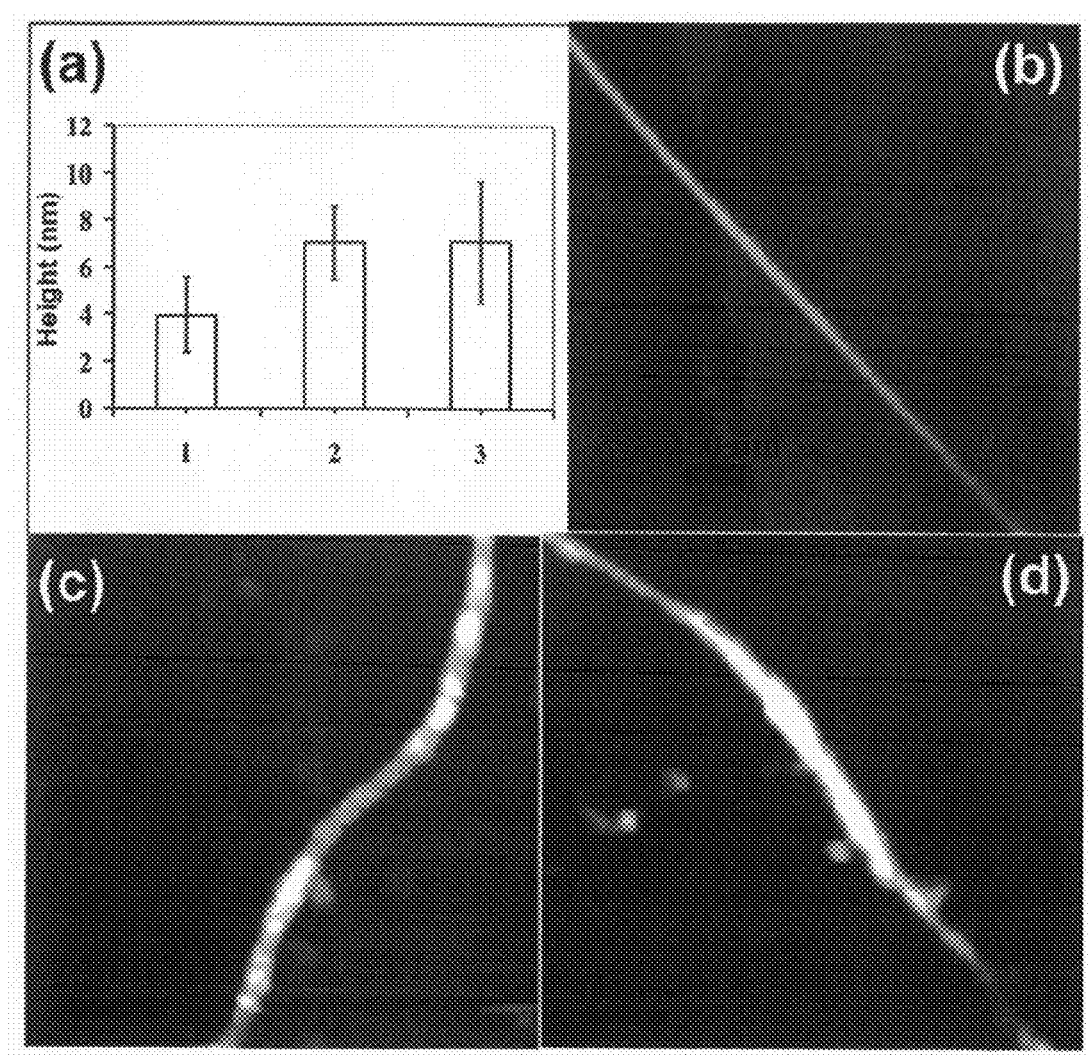
FIG. 3. AFM analysis. (a) Heights of various nanotube samples: (1) SWNT starting material, 3.92±1.58 nm; (2) trimethoxysilane-SWNT adducts, 6.99±1.53 nm; (3) hexaphenyldisilane-SWNT adducts, 7.03±2.56 nm. AFM height images of (b) SWNT starting materials, of (c) hexaphenyldisilane-SWNT adducts, and of (d) trimethoxysilane-SWNT adducts.

Atomic Force Microscopy. In order to determine the precise thickness of the tube coating, a systematic AFM height analysis was undertaken, with averaged height measurements based on >35 bundles of tubes per sample. According to FIG. 3, there is a clear observed increase in thickness of both adducts relative to that of pristine, unreacted nanotubes, which could not be ascribed to nanotube aggregation effects alone. Specifically, the trimethoxysilane-SWNT adduct consisted of a coating with dimensions of 6.99±1.53 nm. The hexaphenyldisilane-SWNT adduct was covered with a layer measuring 7.03±2.56 nm. By contrast, the SWNT starting material possessed an averaged height of 3.92±1.58 nm. A more continuous coating for trimethoxysilane-SWNT adducts was noted as compared with hexaphenyldisilane-SWNT adducts. Since this reaction was carried out on a combination of individual as well as bundles of tubes, it would be expected to see images of non-uniformly functionalized tubes, consisting of localized areas of derivatization exposed by sonication during sample preparation for AFM analysis. In fact, such an unevenly derivatized nanotube structure, manifested as the observation of uneven, disparate heights along selected cross sections distributed along the length of the sample, is observed in FIG. 3d.

Nevertheless, the regions of the nanotube, functionalized with the trimethoxysilane precursor, consisted of a continuous, homogeneous coating, which was effectively uniform in height along the length of the structure, i.e., virtually complete surface functionalization with this particular reaction on a single individual tube. Images observed for the hexaphenyldisilane-SWNT adduct, shown in FIG. 3c, demonstrated functionalization along the nanotube sidewalls but with less uniformity. As a comparison, unreacted tubes are shown in FIG. 3b.

Figure 4:
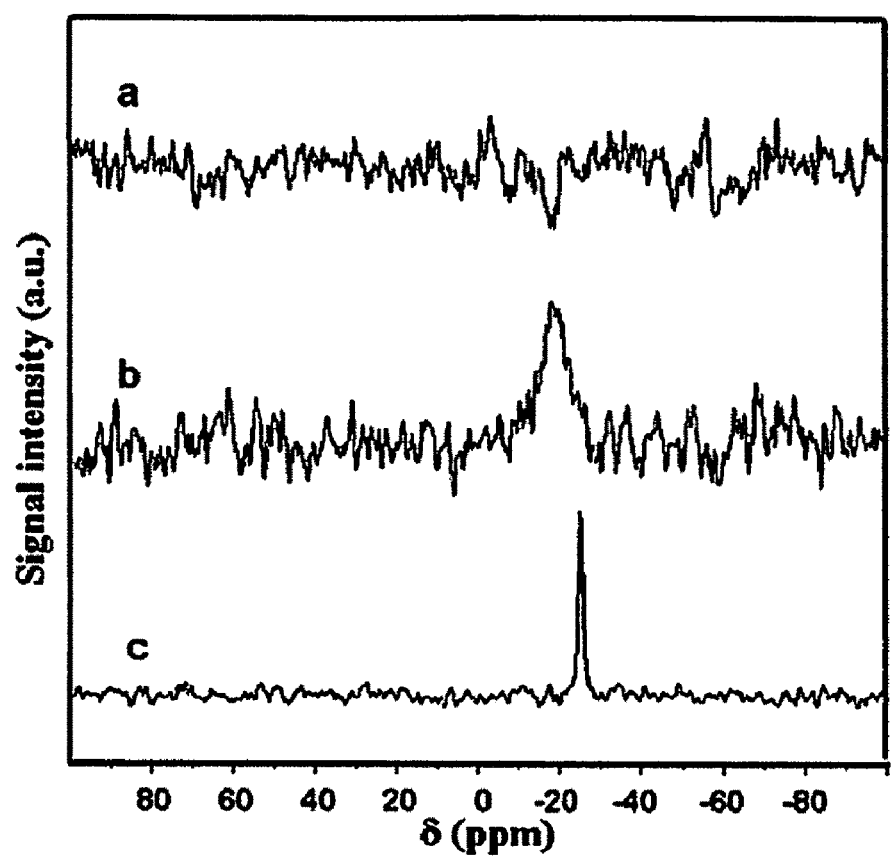
FIG. 4. $^{29}$Si NMR spectroscopy of (a) SWNT starting materials, (b) hexaphenyldisilane-SWNT adducts, and (c) the hexaphenyldisilane precursor.

Silicon NMR Spectroscopy: Solid-state $^{29}$Si NMR spectroscopy was used to characterize the attachment of organosilane precursors to the single-walled carbon nanotube surfaces. As noted in the spectra, in FIGS. 4a and 5a, a signal was not detected for the raw, pristine SWNT starting material. Rather, a sharp signal was seen at −25 ppm for the hexaphenyldisilane precursor (FIG. 4), which was also previously observed by prior literature (T. M. Duncan, *A Compilation of Chemical Shift Anisotropies*, AT&T Bell Laboratories, New Jersey, 1990; Harris et al., *J. Chem. Soc., Faraday Trans.* 1 1989, 85, 1853). Upon attachment to the carbon nanotube, this peak shifted downfield to a higher frequency of −18 ppm and also broadened. Thus, it may be inferred that although the molecular precursor is likely still present, it is no longer present in its original coordination. The nature of the neighboring electronic environment around the Si atom likely altered only slightly though as the chemical shift was on the order of 7 ppm. This observation is consistent with the conversion of a Si—Si bond in the original precursor to a Si—C bond in its coordinative formulation with the carbon nanotube itself. An increase in peak width of the NMR peak is indicative of the localization and immobilization, through restriction of the degrees of conformational freedom, of Si-containing moieties onto surface sites of the tube with an accompanying loss of symmetry.

Figure 5:
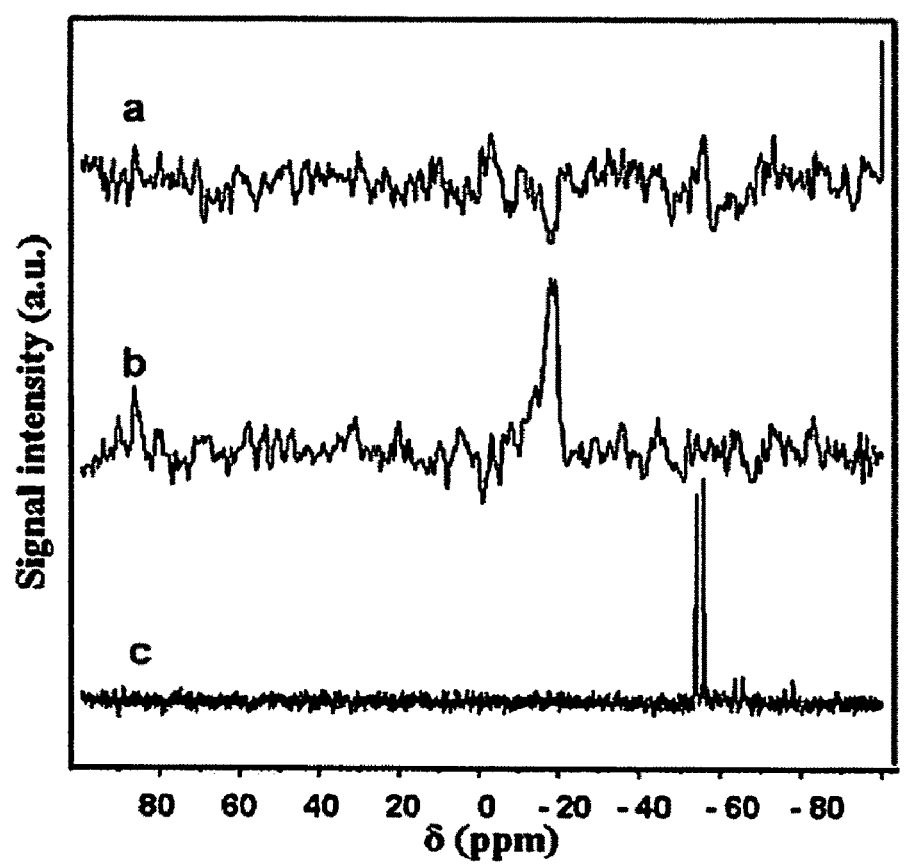
FIG. 5. $^{29}$Si NMR spectroscopy of (a) SWNT starting materials, (b) trimethoxysilane-SWNT adducts, and (c) the trimethoxysilane precursor.

Similar results were noted for the trimethoxysilane precursor, wherein two sharp signals at −54 and −56 ppm merged to form one broad peak at −18 ppm (FIG. 5). The greater shift of 36 ppm noted for this sample likely is an indication of a greater alteration in the silicon environment in this adduct, e.g. the presence of an immobile, cross-linked network. This likely results from the formation of mono-, bi-, and tridentate structures, resulting from reactions involving one, two, and three functional groups of a silane molecule with oxygenated species on the nanotube surface. The possibility that Si—OH is present can be eliminated since the characteristic sharp peak expected at −100 ppm was not observed in any of the spectra (Bauer et al., *Macromol. Chem. Phys.* 2000, 201, 2654). To better probe the exact nature of the chemical change in the SWNTs and the corresponding effect of functionalization on the electronic properties of these tubes, additional spectroscopic methods were employed.

Raman Spectroscopy. Raman spectroscopy is widely used for the characterization of SWNT samples and for gaining information about their structure. It is a particularly powerful probe of electron-phonon coupling and electronic structure in SWNTs. When the incident or scattered photon coincides with an allowed optical transition of a particular nanotube, the Raman spectrum for that tube is considered to be resonantly enhanced. Thus, different lasers bring nanotubes of different diameters into resonance (Rao et al., *Science* 1997, 275, 187). Herein, four excitation wavelengths were used: 488.0 nm (2.54 eV), 514.5 nm (2.41 eV), 632.8 nm (1.96 eV) and 780 nm (1.58 eV). The Raman spectra of SWNTs measured show three important regions: (a) the radial A 1 g breathing mode (RBM) mode (in the 100-500 cm$^{-1}$ region) which is dependent on the diameter of the tube that is brought into resonance, (b) the tangential mode, also known as the G band in the 1515-1590 cm$^{-1}$ region, which is sensitive to charge exchanged between nanotubes and guest atoms that have intercalated into the interstitial channels in tube bundles, and (c) the disorder mode, the D band, which is dispersive in the 1280-1320 cm$^{-1}$ region (Dresselhaus et al., *Acc. Chem. Res.* 2002, 35, 1070).

i. Radial Breathing Modes

Herein is provided an analysis of the intensity of the RBM, which depends on the physical and chemical environment of the SWNTs as well as the degree of bundling in the SWNT sample. It is noted that the radial breathing modes in observed spectra of the functionalized nanotubes contain a strong component of unreacted tubes, as the signals due to the individually reacted tubes themselves mainly either attenuate in intensity or shift in frequency upon silylation.

The radial breathing mode (RBM) frequency can be empirically related to the diameter of the tube using the equation:

$$\omega_{RBM}(\text{cm}^{-1}) = 238/d(\text{nm})^{0.93} \quad (1)$$

Due to the radial nature of the mode in question, the RBM band is particularly affected by the extent of nanotube packing. Hence to account for the intertube van der Waals interactions, equation 1 incorporates a Lennard-Jones potential in addition to a force constant model (Rols et al., *Eur. Phys. J. B* 2000, 18, 201).

Figure 6:
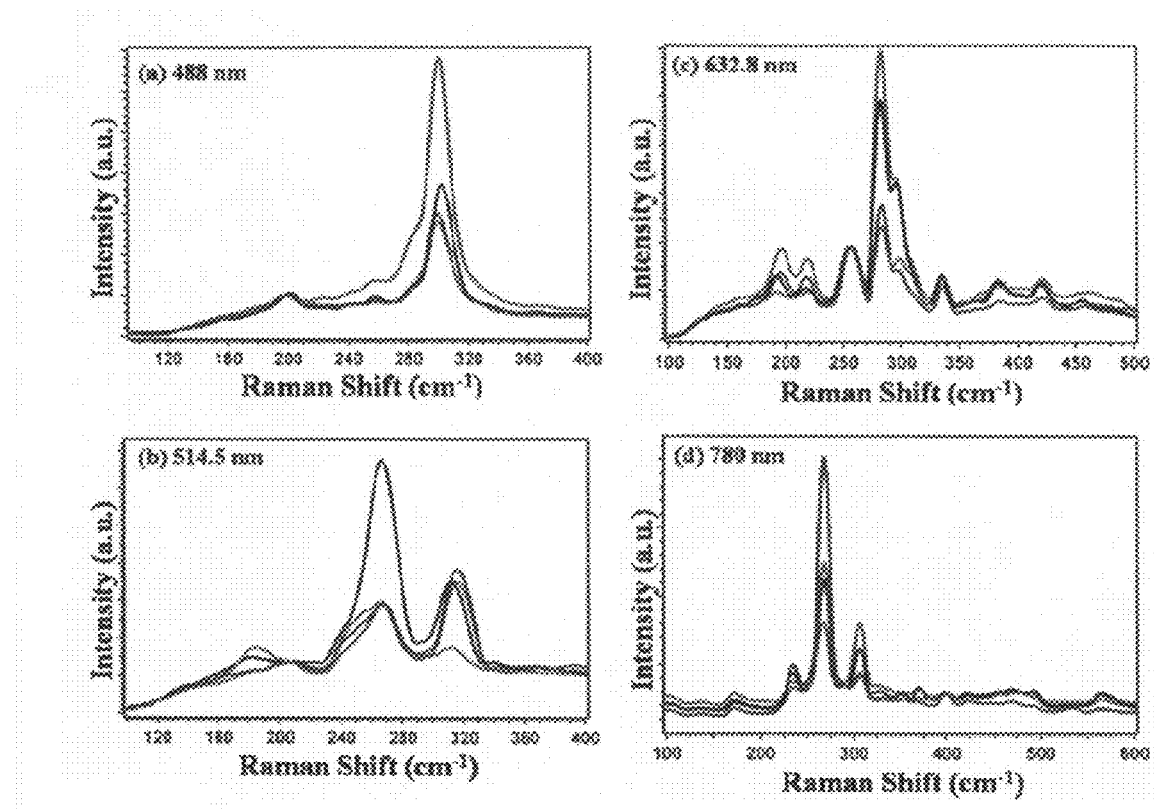
FIG. 6. Raman spectra (RBM region) of pristine CoMoCat SWNTs (black), control samples (green), hexaphenyldisilane-SWNT adducts (blue), and trimethoxysilane-SWNT adducts (red). (a) Excitation at 488 nm with normalization with respect to the RBM feature at 202 cm$^{-1}$. (b) Excitation at 514.5 nm with normalization with respect to the RBM feature at 208 cm$^{-1}$. (c) Excitation at 632.8 nm with normalization with respect to the RBM feature at 256 cm$^{-1}$. (d) Excitation at 780 nm with normalization with respect to the RBM feature at 398 cm$^{-1}$.

Excitation at 632.8 nm brings into resonance both metallic and semiconducting tubes. In FIG. 6c, a number of RBM features above 240 cm$^{-1}$ arise from semiconducting tubes with diameters ranging from 0.92 to 0.52 nm. These features, located at 256, 283, 296, and 335 cm$^{-1}$, have been assigned to (10, 3), (7, 5), (9, 2) and (6, 4) nanotubes, corresponding to diameters of 0.92, 0.84, 0.80, and 0.71 nm, respectively (Jorio et al., *Phys. Rev. B* 2005, 72, 075207). The RBM feature at 192 cm$^{-1}$ has been assigned to (9, 9) metallic nanotubes with an average diameter of 1.22 nm. For trimethoxysilane-SWNT adducts, the larger diameter features are greatly enhanced in intensity upon functionalization, whereas the smaller semiconducting tubes show the opposite trend. Specifically, tubes measuring 0.84 and 0.80 nm in diameter, corresponding to (7, 5) and (9, 2) tubes, respectively, have shown a dramatic decrease in intensity, progressing from the pristine tubes to their functionalized analogues. Thus, the trimethoxysilane precursor showed preferential reactive selectivity for semiconducting tubes measuring 0.84 and 0.80 nm in diameter, with correspondingly less reactivity towards metallic nanotubes.

In analyzing the nature of hexaphenyldisilane-SWNT adducts, it is concluded that this reaction was less diameter-selective. That is, there was a uniform decrease in RBM intensity for features associated with semiconducting nanotubes, an observation indicative of the reactivity of these tubes. Simultaneously, larger-diameter metallic features showed a slight increase in intensity as compared with those of pristine SWNTs, suggestive of some degree of preferential enhancement in the resultant silylated product though the degree to which this occurred was not as great as that observed for the trimethoxysilane-SWNT adduct. Evidently, the results suggest that hexaphenyldisilane reacted to a certain extent with metallic tubes in addition to semiconducting tubes, a conclusion also supported by UV-visible spectroscopy, presented below.

Excitation at 514.5 nm (FIG. 6b) also evinced similar trends. For the trimethoxysilane adduct, a band at 312 cm$^{-1}$, ascribed to 0.76 nm diameter (6, 5) semiconducting tubes, decreased significantly in intensity, while signals at 184 cm$^{-1}$, associated with metallic tubes measuring 1.31 nm in diameter, increased in intensity, showing preferential reactivity for semiconducting tubes. By contrast, from the selective decrease in intensity observed in the lower wavenumber RBM modes (i.e. at 184 cm$^{-1}$), the nanotube adduct, associated with hexaphenyldisilane, showed preferential reactivity of metallic tubes as compared with semiconducting tubes.

The results of excitation at 488 nm are shown in FIG. 6a. The relative intensity of a (9, 2) semiconducting nanotube with a diameter of 0.79 nm, as represented by the 302 cm$^{-1}$ peak, increased in the control spectra and in data associated with the SWNT starting material. A similar trend, namely the observation of the preferential reactivity of semiconducting tubes, for all of these functionalized adducts was observed herein, as well as for data collected at the other excitation wavelengths. That is, in general, a decrease in intensity for the Raman signal associated with functionalized adducts as compared with pristine CoMoCat SWNTs was noted. In addition, a decrease in the signal at 305 cm$^{-1}$ associated with smaller-diameter (8, 3) semiconducting tubes, measuring 0.78 nm in diameter, was observed for both adducts upon excitation at 780 nm (FIG. 6d). Thus, it is concluded from all of these data, that whereas reaction with the hexaphenyldisilane precursor was selective for both smaller-diameter semiconducting and metallic nanotubes, the trimethoxysilane precursor was selective for reaction with certain smaller-diameter semiconducting nanotubes, ranging between 0.78-0.84 nm in diameter.

As mentioned previously, the RBM data are affected by the bundling of the nanotubes in a given sample. Specifically, the peak at 218 cm$^{-1}$ observed at 632.8 nm excitation and the 266 cm$^{-1}$ peak noted upon excitation at both 514.5 nm and 780 nm can provide information about the presence of nanotube bundles. Contrasting behavior among the different types of nanotubes was observed which is likely due to some extent to consequences arising from the effect of UV irradiation. For instance, a slight decrease in the peak intensity for the control samples at these aforementioned wavenumbers, relative to that of pristine CoMoCat tubes, likely indicate slight de-bundling as a result of the UV irradiation. From FIG. 6c, as a result of functionalization with silane derivatives, it is likely that the increase in intensity of the 218 cm$^{-1}$ peak for the adducts as compared with pristine CoMoCat samples is attributable to a bundling effect. The apparent decrease in intensity observed for the 266 cm$^{-1}$ peak at 514.5 nm irradiation concomitant with an increase in intensity at lower wavenumbers has also been ascribed to a bundling or aggregation effect (Karajanagi et al., *Langmuir* 2006, 22, 1392; Heller et al., *J. Phys. Chem. B.* 2004, 108, 6905). By the same token, the apparent increase in intensity observed for the 266 cm$^{-1}$ peak at 780 nm excitation is consistent with bundling of semiconducting tubes (e.g. (7, 6) tubes).

A complicating factor is that the samples were in solid form while under Raman analysis. In solution, the presence of tubular bundles and the extent of debundling will likely vary from that of solid samples as a result of varying intertube interactions induced by effects such as solvation and sonication.

ii. D and G Bands

The tangential G band mode, appearing in the 1400-1700 cm$^{-1}$ region, is related to the Raman-allowed phonon mode, $E_{2g}$, and involves out-of-phase intralayer displacements of the graphene structure of the nanotubes. The G band provides information about the electronic properties of carbon nanotubes. The disorder D band at around 1350 cm$^{-1}$ is related to the presence of defects as well as nanoparticles and amorphous carbon, and usually provides an indication of the level of disordered carbon.

Figure 7:
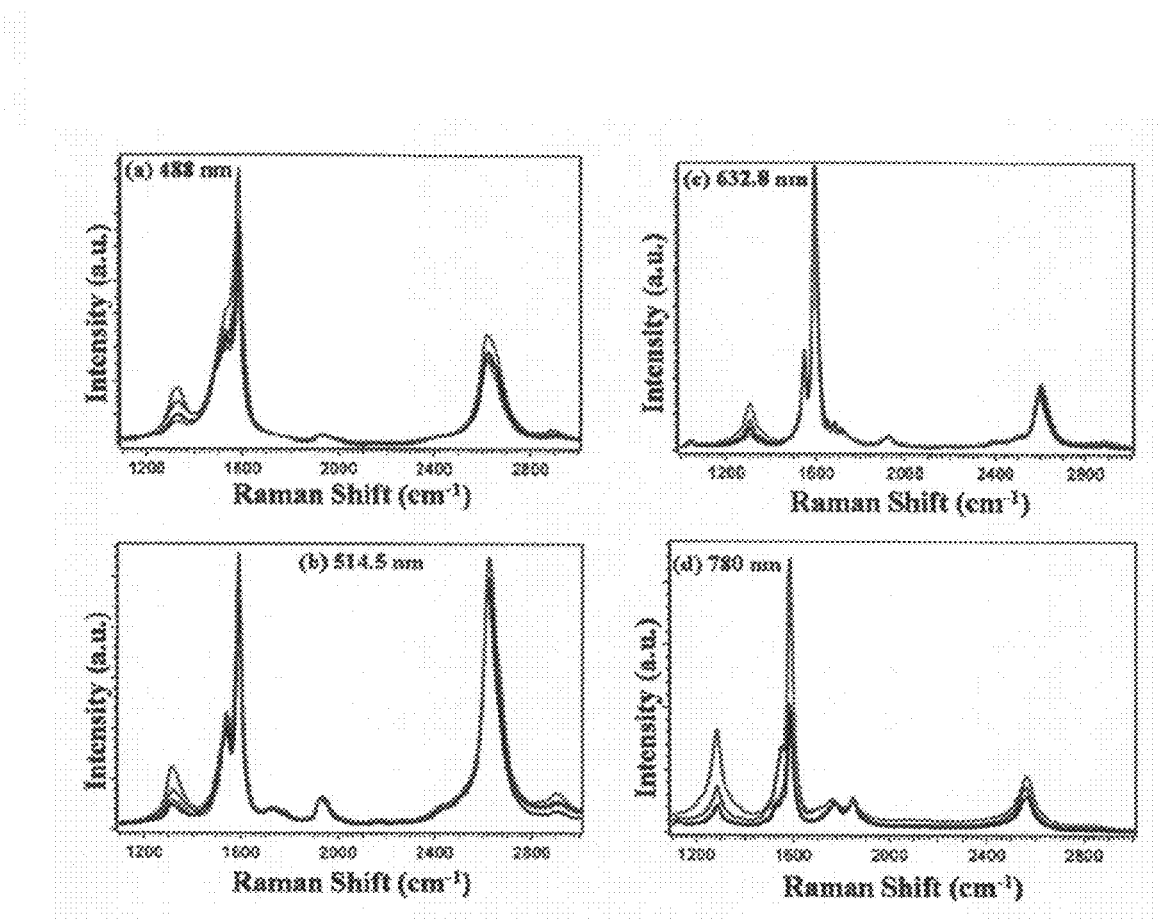
FIG. 7. Raman spectra (D band, G band and G' band regions) for pristine CoMoCat SWNTs (black), control samples (green), hexaphenyldisilane-SWNT adducts (blue), and trimethoxysilane-SWNT adducts (red). Normalization was performed with respect to the feature at around 1940 cm$^{-1}$. Excitation wavelength at (a) 488 nm, (b) 514.5 nm, (c) 632.8 nm, and (d) 780 nm.

The expression, (1−D/G), is used which incorporates the ratio of the D band intensity to the G band intensity, as a measure of nanotube purity, in a similar fashion to protocols utilized by other research groups (Chen et al., *J. Phys. Chem. B.* 2006, 110, 11624; Dillon et al., *Chem. Phys. Lett.* 2005, 401, 522; Vivekchand et al., *Small* 2005, 10, 920). For instance, a low concentration of carbonaceous impurities or imperfections in carbon nanotube samples can be represented by a number close to one. For example, SEM, AFM and HRTEM data show that pristine nanotubes used in these experiments are relatively pure. For example, at 632.8 nm excitation (FIG. 7c), a value of 0.91 was obtained for the pristine samples, while a value of 0.93 was observed for control samples. This slight improvement in sample quality may be attributed to the simple removal of carbonaceous impurities upon exposure to UV lamp irradiation. In addition, this is further indication, along with TEM data, that carbon nanotubes were neither destroyed nor seriously sidewall etched by exposure to UV irradiation alone. The smallest laser power density possible was used during these experiments to prevent damage to the nanotubes.

Calculated values of the expression, (1−D/G), incorporating the D/G intensity ratio, are shown in Table 1, demonstrating similar trends for all excitation wavelengths utilized. It is evident that this expression decreases upon chemical functionalization, i.e. silylation. Moreover, the trimethoxysilane-SWNT adduct showed the smallest value of this expression, implying a greater increase of the D band intensity (and hence greater disorder) relative to hexaphenyldisilane. These results suggest a more effective sidewall functionalization reaction of SWNTs with trimethoxysilane as compared with hexaphenyldisilane, likely through the mediation of added functional groups and extended reactivity at defect sites.

TABLE 1

Mathematical Expression 1 - D/G, Incorporating the Ratio of the Actual D and G Band Intensities of Carbon Nanotube Samples Probed at Different Excitation Wavelengths[a]

| sample | excition wavelengths | | | |
|---|---|---|---|---|
| | 488 nm | 514 nm | 633 nm | 780 nm |
| pristine SWNTs | 0.846 | 0.889 | 0.914 | 0.773 |
| control SWNTs | 0.850 | 0.890 | 0.935 | 0.802 |
| HPD adduct | 0.793 | 0.839 | 0.894 | 0.832 |
| TM adduct | 0.785 | 0.770 | 0.821 | 0.610 |

[a]HPD, hexaphenyldisilane-SWNT adduct, and TM, trimethoxysilane-SWNT adduct.

Analysis of the tangential band offers a method for distinguishing between metallic and semiconducting SWNTs. That is, the peak at 1590 cm$^{-1}$ is associated with a diameter-independent G$^+$ component with A/E$_1$ symmetry. Peaks at 1560 cm$^{-1}$ and 1530 cm$^{-1}$ are respectively associated with the diameter-dependent G$^−$ component for larger-diameter metallic carbon nanotubes (G$^−_M$) and with smaller-diameter semiconducting carbon nanotubes (G$^−_S$) possessing either A or E$_1$ symmetry (Chou et al., *Chem. Phys. Lett.* 2004, 397, 296). Based primarily on data obtained upon excitation at 488 nm and 780 nm, in general, it is noted that peaks corresponding to the G$^−_S$ signal either decreased in intensity or broadened upon silylation, whereas the G$^−_M$ feature was still prominent. This effect was more pronounced for the trimethoxysilane precursor. In conjunction with the RBM data above, these results further confirm that the trimethoxysilane precursor has a greater selectivity for semiconducting nanotubes, ranging around 0.8 nm in diameter.

The strong peak at around 2600 cm$^{-1}$ is known as the G' band in graphite and carbon nanotubes, corresponding to the overtone mode of the D-band (Hishiyama et al., *Phys. Rev. B* 2001, 63, 245406). The origin of the G' band has been theoretically shown as a double resonance, two-phonon Raman process which is independent of the presence of defects (Saito et al., *Phys. Rev. Lett.* 2002, 88, 027401). Changes in the intensity of this peak should be directly related to the D band, which is in fact observed. In most cases, there was an increase in intensity observed for the functionalized adducts as compared with the pristine CoMoCat samples. Shifts of this band have been previously correlated with changes in bond strength upon functionalization (McGuire et al., *Carbon* 2005, 43, 219). The presence of bundling or of localized changes in purity may affect the data.

Figure 8:
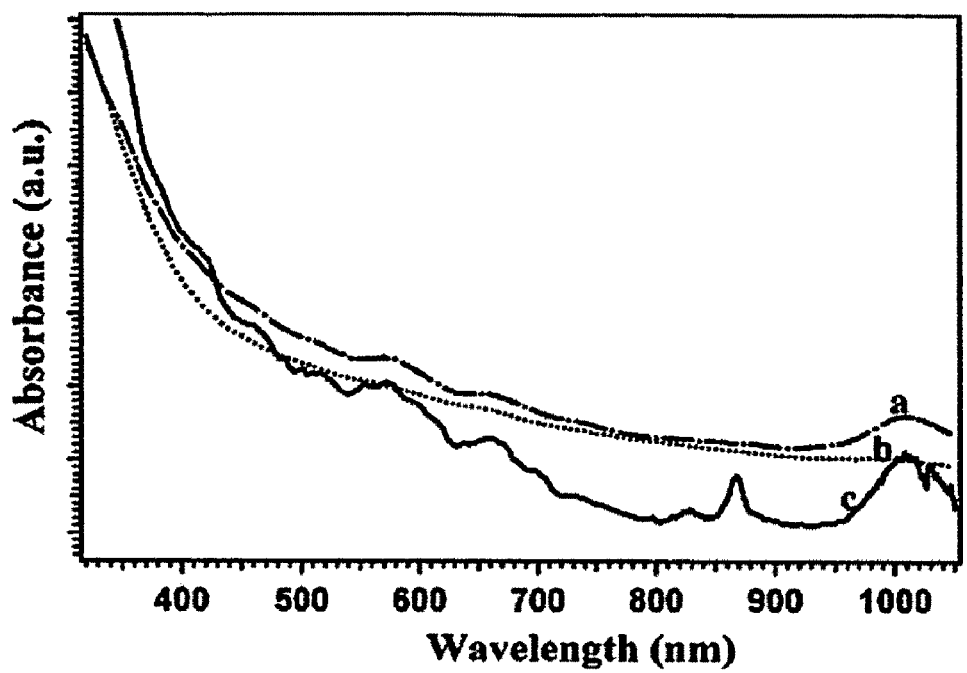
FIG. 8. UV-Visible spectra of (a) trimethoxysilane-SWNT adducts (-•-); (b) hexaphenyldisilane-SWNT adducts (••••); and (c) control samples (-).
Figure 9:
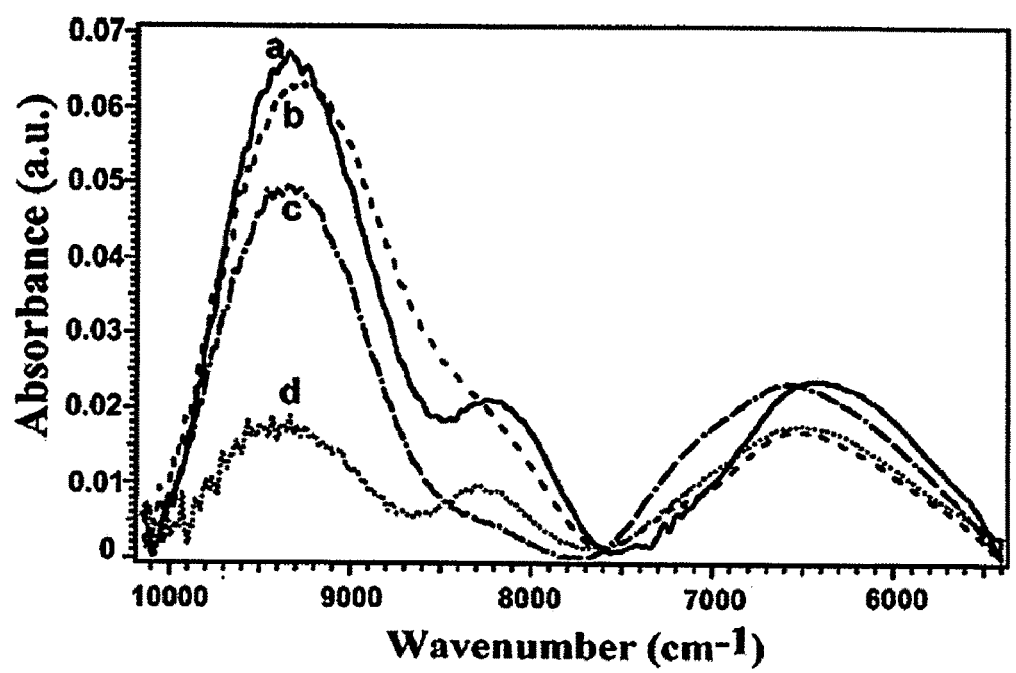
FIG. 9. Near-IR spectra of (a) pristine CoMoCat pristine SWNTs (-); (b) hexaphenyldisilane-SWNT adducts (- - -); (c) control sample (--•--); and (d) trimethoxysilane-SWNT adducts (••••).

UV-Vis-NIR Data Interpretation: Allowable transitions between van Hove singularities in the electronic density of states of SWNTs are observable as spike-like features in the optical spectra of nanotube thin films and solutions (Chen et al., *Science* 1998, 282, 95; Wildoer et al., *Nature* 1998, 391, 59; Bachilo et al., *J. Am. Chem. Soc.* 2003, 125, 11186). These transitions usually occur in the UV-visible-near IR region with their exact position determinant on the diameter of the nanotubes analyzed (Zhang et al., *J. Phys. Chem. B.* 2005, 109, 14375). Only a few sharp absorption peaks were observed in the entire UV-visible-NIR spectrum (FIGS. 8 and 9). Bands corresponding to the metallic SWNT (350-600 nm) were much weaker than those of the semiconducting nanotubes (550-1400 nm). It should be noted that the UV-visible data were collected from solutions and dispersions, obtained by sonication of SWNT samples in DMF followed by centrifugation (Buffa et al., *Macromolecules* 2005, 38, 8258). It also should be emphasized that although surfactants such as sodium dodecyl sulfate are very effective at exfoliating tube bundles, it is still possible to observe transitions in the UV-visible region upon simple sonication in DMF, as was performed in previous reports.

Because SWNTs prepared by most bulk synthesis methods occur as ropes of nanotubes held together by van der Waals forces, their corresponding absorption spectra appear as broad peaks which are, in fact, an aggregate superposition of the absorption spectra of individualized nanotubes of many different diameters and chiralities. Previous reports suggest that there is no preferential suspension of any specific nanotube type upon sonication of pristine CoMoCAT tube samples, since all observed peak intensities increased simultaneously during sonication (Tan et al., *J. Phys. Chem. B.* 2005, 109, 14454).

FIGS. 8 and 9 represent a comparison of CoMoCat pristine SWNTs, of control samples, and of two silane-treated SWNT adducts in the UV-Vis-NIR range. From FIG. 8, in general, it can be concluded that both metallic and semiconducting nanotubes were covalently sidewall functionalized by hexaphenyldisilane, an observation supported by the disappearance of all of the electronic transitions in plot b, with respect to the controls. This loss of transitions in the UV range is indicative of covalent sidewall functionalization, which disrupts the electronic structure of nanotubes. Thus, it is likely that silylation essentially saturates the bond structure on the nanotube sidewalls and introduces defects that perturb and destroy the intrinsic periodicity of the conjugated sp$^2$-hybridized nanotube electronic structure (Kamaras et al., *Science* 2003, 301, 1501).

The reaction with trimethoxysilane demonstrated a more selective sidewall functionalization for specific semiconducting nanotubes. This was seen from the conservation of metallic features (FIG. 8, plot a) after functionalization, indicative of minimum reactivity towards these tubes. Specifically, there was likely selective functionalization of (5, 4) semiconducting tubes, measuring 0.620 nm in diameter, as demonstrated by the complete disappearance of the 868 nm peak. In addition, the peak at 828 nm, corresponding to (7, 2) semiconducting tubes, measuring 0.650 nm in diameter, also diminished in intensity (Weisman et al., *Nano Lett.* 2003, 3, 1235). Features at 1008 nm and 567 nm, which can be ascribed to (6, 5) semiconducting tubes of diameter 0.76 mm, also decreased to some extent in intensity, indicative of their intrinsic reactivity, corroborating the Raman data discussed previously. Thus, taken collectively, these results show that the reaction with trimethoxysilane is particularly selective for certain smaller diameter semiconducting nanotubes measuring 0.62, 0.65, 0.76, 0.78, 0.79, 0.80 and 0.84 nm in diameter, while hexaphenyldisilane is reactive towards both semiconducting and metal nanotubes. In addition, the presence of more prominent peaks in the trimethoxysilane adduct spectrum suggests a de-bundling effect in solution, which likely account for the increased stability of these functionalized tubes in DMF solution (available as Si at http://pubs.acs.org) (Karajanagi et al, *Langmuir* 2006, 22, 1392).

In FIG. 9, the major bands observed correspond to $S_{11}$ and $S_{22}$ transitions between the first and second pairs of van Hove singularities for semiconducting nanotubes. The band at 9345 cm$^{-1}$ is consistent with that of $S_{22}$ transitions observed for tubes with calculated diameters close to 1.5 nm of the (15, 7) type (Weisman et al., *Nano Lett.* 2003, 3, 1235). Bands have also been noted at around 8192 cm$^{-1}$ and 6423 cm$^{-1}$, respectively, corresponding to $S_{22}$ and $S_{11}$ transitions of tubes measuring 1.86 nm and 1.35 mm in diameter, respectively. By comparing the relative intensity of the 9345 and 6423 cm$^{-1}$ peaks, it can be seen that there was selectivity for 1.5 nm semiconducting tubes in the reaction with trimethoxysilane, since the $S_{22}$ peak for these tubes decreased significantly in intensity with respect to the $S_{11}$ transition. By contrast, the reaction with the hexaphenyldisilane did not appear to have obviously disrupted these particular transitions. Thus, again, coupled with a significant weakening of the $M_{11}$ transition, the data support the selectivity of the reaction with the trimethoxysilane precursor for predominantly semiconducting nanotubes.

Mid-IR data interpretation. In order to better understand the chemical nature of the attachment mechanism of silanes onto the SWNT surface, mid-IR spectra were obtained. Mid-IR spectroscopy was used to investigate the identity of functionalities on the carbon nanotube surface. As observed in the spectrum of pristine tubes (FIG. 10a), the C═C peak at 1566 cm$^{-1}$ could be attributed to the carbon skeleton in-plane $E_{1u}$ stretch of the nanotubes (Hemraj-Benny et al., *Chem. Mater.* 2004, 16, 1855). Although these nanotubes were not intentionally functionalized with oxygenated groups through a protocol such as an acid treatment, the presence of surface oxygenated functionalities was nonetheless noted. For example, the peak at 1693 cm$^{-1}$ can be assigned to the carbonyl (C═O) stretching vibration, associated with ketones, aldehydes, or carboxylic acid groups, whereas the peak at 1253 cm$^{-1}$ corresponds to a C—O stretch. Other features, such as that at 1000 cm$^{-1}$, are likely attributed to the carbon ring breathing mode and C—H bending. It should also be noted that similar spectral features were observed both in pristine and control samples. These observations further confirm that spectral band alterations changes, observed with the adduct's IR spectra, likely had chemical origins, associated with the silane reaction itself, as opposed to unrelated, external, physical stimuli such as exposure to UV irradiation.

Figure 10:
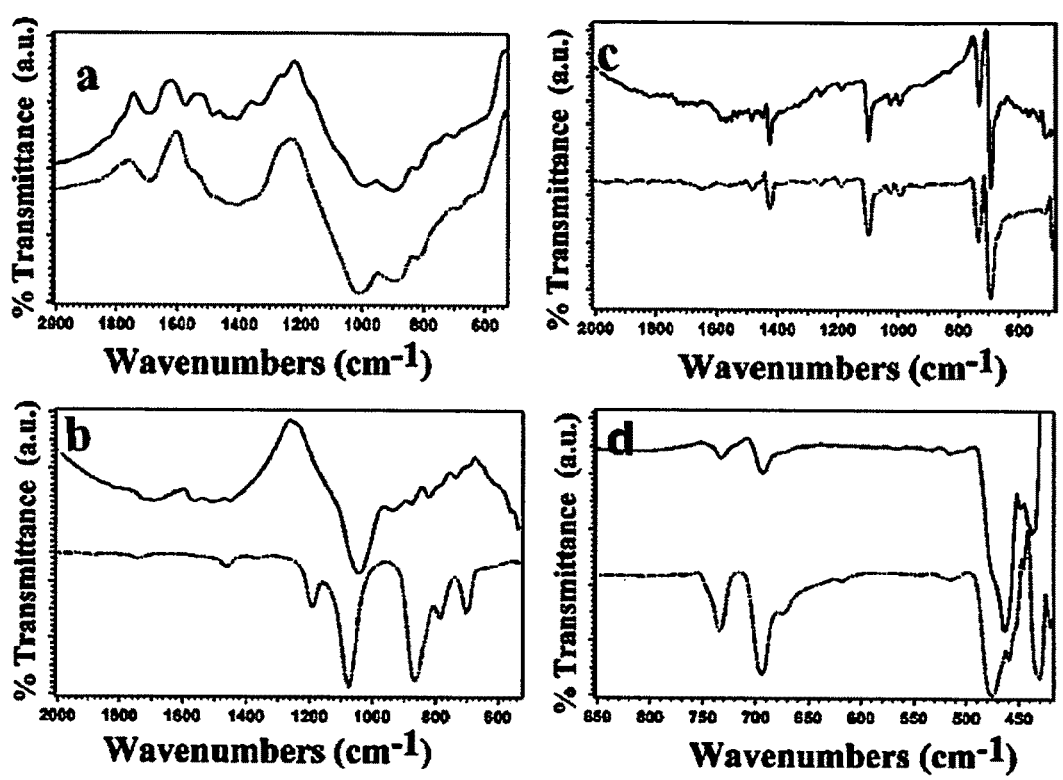
FIG. 10. Mid-IR spectra of (a) pristine CoMoCat SWNTs (-) and of control samples (--••--); (b) and (d) of hexaphenyldisilane-SWNT adducts (-) and hexaphenyldisilane precursor (- -••--) in different wavenumber regions; (c) of trimethoxysilane-SWNT adducts (-) and trimethoxysilane precursor (--••--).

FIG. 10, part b illustrates spectra for the trimethoxysilane precursor and the trimethoxysilane-SWNT adduct, respectively. The 1457 cm$^{-1}$ peak, representing the antisymmetric methyl deformation, can be observed in both spectra, indicating that methyl groups were still attached to silicon upon coordination to the carbon nanotubes. The 1074 cm$^{-1}$ peak, initially observed in the precursor spectrum, can be ascribed to the Si—O—C stretch and shifted to 1037 cm$^{-1}$ in the carbon nanotube adduct (Lambert et al., *Organic Structural Spectroscopy*, Prentice Hall, Upper Saddle River, N.J., 1998). In addition, the associated peak width increased in magnitude. The Si—O—C deformation peak, initially observed at 787 cm$^{-1}$ in the precursor spectrum, presumably was displaced to 737 cm$^{-1}$. As the prominent Si—H deformation peak observed at 866 cm$^{-1}$ in the trimethoxysilane precursor spectrum in FIG. 10b significantly reduced in intensity with respect to the 1074 cm$^{-1}$ peak in the adduct spectrum, this result is consistent with the removal of the proton itself upon attachment to the SWNTs. It can also be assumed that no unreacted trimethoxysilane precursor was present in the adduct sample, since no discernible Si—H peak at 866 cm$^{-1}$ was observed in the adduct spectrum. In addition, the fact that a Si—O—C peak was noted in the adduct spectrum suggested that hydrolysis of the methoxy groups likely did not occur. Moreover, to confirm this point, no Si—OH vibrations at 798 and 956 cm$^{-1}$ were detected, as noted in previous reports (Velasco-Santos et al., *Nanotechnology* 2002, 13, 495).

Spectra in FIG. 10, part c and d, represent the hexaphenyldisilane precursor and the hexaphenyldisilane-SWNT adduct, respectively, in two complementary spectral ranges. The first conclusion that can be drawn from the plots in part c is that most of the features noted in the precursor spectrum can be seen in the corresponding adduct. Specifically, the 1484 cm$^{-1}$ peak represents the aromatic ring C=C stretch of the phenyl rings, whereas the 1190 cm$^{-1}$ and 732 cm$^{-1}$ peaks represent the C—H in-plane bending and out-of-plane bending, respectively (Lambert et al., *Organic Structural Spectroscopy*, Prentice Hall, Upper Saddle River, N.J., 1998). In addition, a very sharp 695 cm$^{-1}$ peak can be attributed to out-of-plane C—H deformations of the phenyl rings. Since these features can be observed for both the hexaphenyldisilane precursor and its corresponding functionalized adduct, it can be assumed that if in fact the silane precursor is attached to the carbon nanotube surface, the phenyl groups remain effectively attached to the silicon atom. That is, the hexaphenyldisilane precursor did not totally fragment. Additional evidence for this assertion can be corroborated by the presence of Si—C stretch signals at 1257 cm$^{-1}$ and at 1099 cm$^{-1}$ in both spectra.

Mid-IR evidence also indicated the cleavage of the Si—Si bond, as can be seen in FIG. 10, part d where the Si—Si bond peak at 430 cm$^{-1}$ decreased significantly with respect to that of the 475 cm$^{-1}$ peak (K. Nakamato, *Infrared and Raman Spectra of Inorganic and Coordination Compounds, Vol. Part A*, 5th ed., John Wiley & Sons, Inc, Canada, 1997). The 475 cm$^{-1}$ peak, representing the in-plane and out-of-plane ring deformations, shifted slightly downfield with a change in its features (Lambert et al., *Organic Structural Spectroscopy*, Prentice Hall, Upper Saddle River, N.J., 1998). These observations are consistent with the idea of attachment of molecules to the carbon nanotube sidewalls and associated defect sites. It should also be noted that features such as the C=C stretch at 1566 cm$^{-1}$ for the carbon nanotube framework were observed in the spectra of both the silane and its accompanying nanotube adduct and that silicon dioxide was not detected.

XPS analysis. To further confirm the above data, X-ray photoelectron spectroscopy (XPS) was used to provide information about the chemical composition and bonding of the carbon nanotube-silane adducts. Table 2 shows the estimated atomic concentration of carbon, oxygen, and silicon in the starting materials and in the associated adducts.

TABLE 2

XPS Data of the Estimated Atomic Concentrations (in %) of Species Attached to SWNTs within a 2-4 nm Top Surface Analyzed Layer$^a$

| | estimated atomic concentrations (%) | | |
|---|---|---|---|
| sample | C | O | Si |
| CoMoCAT SWNTs | 78.67 | 11.20 | 2.22 |
| control SWNTs | 89.14 | 5.19 | |
| HPD adduct | 87.24 | 10.54 | 1.55 |
| TM adduct | 52.29 | 34.36 | 7.29 |

$^a$HPD, hexaphenyldisilane-SWNT adduct, and TM, trimethoxysilane-SWNT adduct.

As confirmed by IR data, there were a number of oxygenated functionalities such as C—O, C=O, and O—C=O groups present on the surfaces of CoMoCat nanotubes. Exact percentages are available as SI at http://pubs.acs.org. The increased oxygen concentration observed for the trimethoxysilane-SWNT adducts can be attributed to the presence of the silane derivative. In addition, there was silicon present in the initial CoMoCat carbon nanotube sample. After base treatment, the sample silicon content decreased to an estimated zero percent, as previously suggested by EDS. Thus, the presence of silicon in the functionalized adduct could be associated with the silane derivative, as predicted.

Hence, based on the mid-IR data and the XPS high resolution data (available as SI at http://pubs.acs.org), it is concluded that with the trimethoxysilane-SWNT adduct, the precursor could attach to the carbon nanotube surface by means of oxygenated groups, through which a Si—O—Si scaffolding framework and associated coating could form. In other words, as suggested by XPS, the binding energy of 100.61 eV can be attributed to the actual binding of SiO to the carbon nanotube (SiO—$C_{NT}$), whereas the binding energy at 103.30 eV can be plausibly ascribed to a siloxane network (Si—O—Si) (Vast et al., *Nanotechnology* 2004, 15, 781). Although it is possible that the methyl groups were completely removed in the reaction, it is known from mid-IR data that some of the methyl groups were still present in the functionalized adduct. Hence, the shift and broadening in the Si—O—C peak observed in the adduct could actually have been attributed to the presence of two types of Si—O—C bonding, namely a Si—O—C bond in the precursor as well as a Si—O—$C_{NT}$ bond. In the latter case, methyl groups were removed, allowing the oxygen to react with the C=C carbon nanotube framework. There is nothing to discount the possibility of trimethoxysilane precursor itself undergoing bonding with the Si—O—Si surface. This scenario is in agreement with observations noted in $^{29}$Si NMR data, implying the formation of mono-, bi-, and tridentate structures, resulting from reactions involving one, two, and three functional groups of a silane molecule with oxygenated species on the nanotube surface. In addition, the increase in the Raman D band intensity observed for the adducts is consistent with this type of attack of the C=C framework.

The reaction of SWNTs with hexaphenyldisilane was likely somewhat milder with cleaving of the reagent molecule followed by attachment through the oxygen-decorated ends and defect sites of the nanotubes as well as nanotube sidewalls. As with the trimethoxysilane adduct, a peak corresponding to a binding energy of 100.92 eV was observed and could be attributed to the binding of SiO to the carbon nanotube (SiO—$C_{NT}$). As the UV-visible data indicated, there was a degree of perturbation of the electronic structure as a result of sidewall functionalization but the slight increase in the D band in the Raman data suggested this was not overly significant. Consistent with the mid-IR data, phenyl groups arising from the reagent were still present in the SWNT adduct upon attachment.

While not wanting to be bound by a theory, a proposed mechanism of attachment of the individual silane precursors can be postulated. Specifically, for the trimethoxysilane adduct, it can be assumed that the proton was removed by the platinum catalyst, activated by the UV irradiation allowing attachment (to some extent) of the —Si(OCH$_3$)$_3$ not only to (1) the carbon nanotube C=C framework but also to (2) oxygenated functionalities onto the ends as well as defect sites along the sidewalls of the nanotubes. Based on XPS and NMR data, a loss of the methyl groups from the precursor would allow for formation of an intermolecular —Si—O—Si— network with the attached —SiO groups forming the coating observed by microscopy. The presence of this coating may also account for the increased solubility and stability observed for this adduct as compared with the adduct derived from the hexaphenyldisilane reaction. A proposed representation of this reaction schematic can be observed in Scheme 2 (FIG. 12).

By comparison, for the hexaphenyldisilane adduct, XPS data suggested the likelihood of Si attachment to the actual carbon nanotube framework, more specifically to the oxygenated functionalities at the ends and defect sites of the nanotubes. Therefore, it can be hypothesized, as also corroborated by IR and NMR data, that the Si—Si bond breaks upon UV irradiation to facilitate attachment of the —Si(Ph)$_3$ groups to the oxygenated groups on the nanotube framework. Possible scenarios regarding moiety attachment are noted in Scheme 2 (FIG. 12).

In general, nanotubes can be effectively silylated with both trimethoxysilane and hexaphenyldisilane precursors. The trimethoxysilane precursor is selectively more reactive towards semiconducting nanotubes than metallic nanotubes. This observation is likely a consequence of the fact that the majority of semiconducting nanotubes observed, as shown through Raman data in particular, possessed generally smaller diameters. Smaller-diameter tubes are more reactive than larger-diameter tubes towards silylation. The fundamental point to note is that the present invention provides placing coatings of dielectric materials onto nanotubes ends and sidewalls through a well-defined, relatively mild molecular reaction, which is structurally non-destructive to the nanotube itself.

The invention claimed is:

1. An adduct comprising a carbon nanotube with at least one covalently attached silane moiety, wherein the silicon atom of the silane moiety is directly attached to the carbon nanotube, or is attached to an oxygenated functionality on the carbon nanotube, wherein about 3% to 30% of the sidewall carbon atoms of the nanotube have a silane moiety attached, and wherein the silane moiety is trimethoxysilane; hexaphenyldisilane; silylphosphine; 1,1,1,3,5,5,5-heptamethyltrisiloxane; polydimethylsiloxane, poly(N-bromobenzene-1,3-disulfonamide); N,N,N',N'-tetrabromobenzene-1,3-disulfonamide; hexamethyldisilazane (HMDS); chlorotrimethylsilane (TMCS); trichloromethylsilane (TCMS); an alkyl(alkylamino)silane; a tri(alkoxy)silane; R1SiHR2R3, wherein R1-R3 is a substituted or unsubstituted hydrocarbyl with 1-10 carbon atoms; tert-butyldimethylsilane; monochloroaminosilane; dichloroaminosilane; trichloroaminosilane; or dimethylaminosilane.

2. The adduct of claim 1 comprising a carbon nanotube with covalently attached trimethoxysilane (TM) moieties.

3. The adduct of claim 1 comprising a carbon nanotube with covalently attached hexaphenyldisilane (HPD) moieties.

4. The adduct of claim 1 wherein the range of the quantity of sidewall carbon atoms of the nanotube that have a silane moiety attached has a lower boundary of approximately 3%, 5%, 8%, 10% or 12%.

5. The adduct of claim 1 wherein the range of the quantity of sidewall carbon atoms that have a silane moiety attached has an upper boundary of approximately 30%, 25%, 20% or 16%.

6. The adduct of claim 1 wherein the nanotube is a SWNT.

7. The adduct of claim 1 wherein the nanotube is a MWNT.

8. The adduct of claim 1 wherein the nanotube is semiconducting.

9. A method of functionalizing a plurality of carbon nanotubes with silane moieties, the method comprising:
    contacting a carbon nanotube dispersion with a silane moiety to form a precursor mixture, and
    irradiating the precursor mixture to functionalize the nanotubes with silane moieties, wherein about 3% to 30% of the sidewall carbon atoms of the nanotube are functionalized with a silane moiety.

10. The method of claim 9 wherein the silane moiety is trimethoxysilane; hexaphenyldisilane; silylphosphine; 1,1,1,3,5,5,5-heptamethyltrisiloxane; polydimethylsiloxane, poly(N-bromobenzene-1,3-disulfonamide); N,N,N',N'-tetrabromobenzene-1,3-disulfonamide; hexamethyldisilazane (HMDS); chlorotrimethylsilane (TMCS); trichloromethylsilane (TCMS); an alkyl(alkylamino)silane; a tri(alkoxy)silane; R1SiHR2R3, wherein R1-R3 is a substituted or unsubstituted hydrocarbyl with 1-10 carbon atoms; tert-butyldimethylsilane; monochloroaminosilane; dichloroaminosilane; trichloroaminosilane; or dimethylaminosilane.

11. The method of claim 9 further comprising isolating functionalized adducts.

12. The method of claim 9 further comprising flushing the carbon nanotube dispersion with argon and/or contacting the carbon nanotube dispersion with extra dry 2-propanol before exposure to the silane moiety.

13. The method of claim 9 wherein the silane moiety is trimethoxysilane and wherein the carbon nanotube dispersion is further contacted with a transitional metal catalyst to form the precursor mixture.

14. The method of claim 13 wherein the amount by weight of the nanotube dispersion to the amount by weight of the trimethoxysilane is from about 1:1 to about 1:50.

15. The method of claim 9 wherein the silane moiety is hexaphenyldisilane.

16. The method of claim 15 wherein the amount by weight of the nanotube dispersion to the amount by weight of the hexaphenyldisilane is from about 1:1 to about 1:50.

17. A method of providing single SWNTs with diameters less than a selected diameter, the method, comprising:
    contacting a carbon nanotube dispersion with silane moieties to form a precursor mixture;

irradiating the precursor mixture whereby SWNTs with diameters less than the selected diameter are functionalized with silane moieties; and precipitating the SWNTs functionalized with silane moieties from the mixture, wherein single SWNTs with diameters less than the selected diameter are provided, wherein about 3% to 30% of the sidewall carbon atoms of the SWNTs have a silane moiety attached.

18. A method of functionalizing a plurality of carbon nanotubes with silane moieties, the method comprising:

contacting a carbon nanotube dispersion with a silane moiety to form a precursor mixture; and irradiating the precursor mixture to functionalize the nanotubes with silane moieties, wherein the silane moiety is trimethoxysilane or hexaphenyldisilane.

19. The method of claim 18 wherein the amount by weight of the nanotube dispersion to the amount by weight of the silane moiety is from about 1:1 to about 1:50.

20. The method of claim 18 wherein the carbon nanotube dispersion is further contacted with a transitional metal catalyst to form the precursor mixture.

* * * * *